(12) United States Patent
Yoshikawa et al.

(10) Patent No.: US 9,713,584 B2
(45) Date of Patent: Jul. 25, 2017

(54) INTERNAL OLEFIN SULFONATE COMPOSITION AND CLEANSING COMPOSITION CONTAINING SAME

(71) Applicant: KAO CORPORATION, Tokyo (JP)

(72) Inventors: Yohei Yoshikawa, Wakayama (JP); Yoshinori Mitsuda, Wakayama (JP); Hiroshi Hori, Wakayama (JP); Yoshifumi Nishimoto, Wakayama (JP); Yasuhiro Doi, Kainan (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/417,079

(22) PCT Filed: Sep. 19, 2013

(86) PCT No.: PCT/JP2013/076174
§ 371 (c)(1),
(2) Date: Jan. 23, 2015

(87) PCT Pub. No.: WO2014/046301
PCT Pub. Date: Mar. 27, 2014

(65) Prior Publication Data
US 2015/0202134 A1    Jul. 23, 2015

(30) Foreign Application Priority Data

Sep. 20, 2012  (JP) ................................ 2012-207570
Jun. 25, 2013  (JP) ................................ 2013-132314

(51) Int. Cl.
| | |
|---|---|
| A61K 8/46 | (2006.01) |
| A61Q 5/02 | (2006.01) |
| A61Q 19/10 | (2006.01) |
| A61K 8/44 | (2006.01) |
| A61Q 5/12 | (2006.01) |
| A61K 8/73 | (2006.01) |

(52) U.S. Cl.
CPC ............... *A61K 8/466* (2013.01); *A61K 8/44* (2013.01); *A61K 8/442* (2013.01); *A61K 8/46* (2013.01); *A61K 8/731* (2013.01); *A61K 8/732* (2013.01); *A61K 8/737* (2013.01); *A61Q 5/02* (2013.01); *A61Q 5/12* (2013.01); *A61Q 19/10* (2013.01); *A61K 2800/5424* (2013.01); *A61K 2800/5426* (2013.01); *A61K 2800/5428* (2013.01); *A61K 2800/596* (2013.01)

(58) Field of Classification Search
CPC ........... A61K 8/466; A61Q 5/02; A61Q 19/10
USPC ....................................................... 510/127
See application file for complete search history.

(56) References Cited

U.S. PATENT DOCUMENTS

| | | | | |
|---|---|---|---|---|
| 3,332,878 A | * | 7/1967 | Coward ................... | C11D 1/12 510/237 |
| 3,708,437 A | * | 1/1973 | Sweeney ................ | C11D 3/046 510/237 |
| 3,808,157 A | | 4/1974 | Dewitt et al. | |
| 4,028,283 A | * | 6/1977 | Murata ................... | C11D 1/12 510/351 |
| 4,075,129 A | | 2/1978 | Murata et al. | |
| 4,220,548 A | | 9/1980 | Hashimoto et al. | |
| 4,507,223 A | * | 3/1985 | Tano ...................... | C09K 8/584 507/259 |
| 4,555,351 A | * | 11/1985 | Morita ................... | C09K 8/584 166/270.1 |
| 4,589,988 A | | 5/1986 | Rieck et al. | |
| 4,597,879 A | * | 7/1986 | Morita ................... | C09K 8/584 166/270.1 |
| 4,715,991 A | | 12/1987 | Hirakouchi et al. | |
| 4,852,653 A | * | 8/1989 | Borchardt .............. | C09K 8/592 166/270.1 |
| 4,925,976 A | | 5/1990 | Terao et al. | |

(Continued)

FOREIGN PATENT DOCUMENTS

| | | | | |
|---|---|---|---|---|
| CA | 1338239 C | * | 4/1996 | ........... C07C 303/06 |
| CN | 86 1 02800 A | | 1/1987 | |

(Continued)

OTHER PUBLICATIONS

International Search Report and Written Opinion of the International Searching Authority dated Mar. 20, 2013, for International Application No. PCT/JP2013/076176.

(Continued)

*Primary Examiner* — Nicole M Buie-Hatcher
*Assistant Examiner* — M. Reza Asdjodi
(74) *Attorney, Agent, or Firm* — Birch, Stewart, Kolasch & Birch, LLP

(57) ABSTRACT

Provided is an internal olefin sulfonate composition which is capable of exerting good foamability together with good volume of foam, foaming speed, foam dissipation property, foam quality, foam durability in the presence of sebum, and volume of foam in the presence of sebum at high levels, and a cleansing composition containing the same. The internal olefin sulfonate composition of the present invention comprises (A) an internal olefin sulfonate having 16 carbon atoms and (B) an internal olefin sulfonate having 18 carbon atoms, wherein a mass content ratio (A/B) of component (A) to component (B) is from 75/25 to 90/10, and wherein a mass ratio (hydroxy form/olefin form) of a content of a hydroxy form in the internal olefin sulfonate of the component (A) and the component (B) to a content of an olefin form in the internal olefin sulfonate of the component (A) and the component (B) is from 75/25 to 100/0.

16 Claims, No Drawings

(56) References Cited

U.S. PATENT DOCUMENTS

| | | | |
|---|---|---|---|
| 5,078,916 A * | 1/1992 | Kok | C11D 1/143 |
| | | | 510/488 |
| 5,580,494 A | 12/1996 | Sandhu et al. | |
| 5,876,705 A | 3/1999 | Uchiyama et al. | |
| 6,156,297 A | 12/2000 | Maurin et al. | |
| 6,184,190 B1 | 2/2001 | D'Ambrogio et al. | |
| 6,403,654 B1 | 6/2002 | De Oliveira | |
| 6,586,379 B1 | 7/2003 | Seipel | |
| 6,656,454 B1 | 12/2003 | Koester et al. | |
| 2002/0146442 A1 | 10/2002 | Sendelbach et al. | |
| 2007/0031362 A1 | 2/2007 | Kreeger et al. | |
| 2011/0039744 A1 | 2/2011 | Heath et al. | |
| 2012/0058067 A1 | 3/2012 | Van Gogh et al. | |
| 2012/0270764 A1 | 10/2012 | Brown et al. | |
| 2013/0252855 A1* | 9/2013 | Weerasooriya | C09K 8/584 |
| | | | 507/202 |
| 2014/0079658 A1 | 3/2014 | Terazaki et al. | |
| 2014/0080747 A1 | 3/2014 | Hirahara et al. | |
| 2015/0202134 A1* | 7/2015 | Yoshikawa | A61K 8/466 |
| | | | 510/127 |

FOREIGN PATENT DOCUMENTS

| | | | |
|---|---|---|---|
| CN | 1039803 A | | 2/1990 |
| EP | 0 377 261 A2 | | 7/1990 |
| EP | 0351928 B1 | | 6/1993 |
| JP | 49-078706 A | | 7/1974 |
| JP | 54-134711 A | | 10/1979 |
| JP | 55-043138 A | | 3/1980 |
| JP | 55-056196 A | | 4/1980 |
| JP | 56-167799 A | | 12/1981 |
| JP | 59-27995 A | | 2/1984 |
| JP | 59-222466 A | | 12/1984 |
| JP | 61-134366 A | | 6/1986 |
| JP | 61-45964 B2 | | 10/1986 |
| JP | 1-151510 A | | 6/1989 |
| JP | 1-272564 A | | 10/1989 |
| JP | 2003-81935 A | | 3/2003 |
| JP | 2003081935 A | * | 3/2003 |
| JP | 2003-183152 A | | 7/2003 |
| JP | 2006-527785 A | | 12/2006 |
| JP | 2007-15940 A | | 1/2007 |
| JP | 2009-256211 A | | 11/2009 |
| WO | WO 2014/046175 A1 | | 3/2014 |
| WO | WO 2014/046176 A1 | | 3/2014 |

OTHER PUBLICATIONS

International Search Report and Written Opinion of the International Searching Authority dated Mar. 20, 2014, for International Application No. PCT/JP2013/076171.
International Search Report and Written Opinion of the International Searching Authority dated Mar. 20, 2014, for International Application No. PCT/JP2013/076172.
International Search Report and Written Opinion of the International Searching Authority dated Mar. 20, 2014, for International Application No. PCT/JP2013/076173.
International Search Report and Written Opinion of the International Searching Authority dated Mar. 20, 2014, for International Application No. PCT/JP2013/076174.
Kosswig et al., "Surfactants", Wiley-VCH Verlag GmbH & Co. KGaA, Weinheim, 2005, XP002554753, pp. 1-76.
Kao Corporation, "Kaoakypo RLM-45NV", Product Specification for Sodium Laureth-6 Carboxylate, retrieved online on Dec. 6, 2016, 1 page.
Wikihow, "How to Shampoo and Condition Your Hair," https://web.archive.org/web/20090418054258/http://www/wikihow.com/Shampoo-and-C . . . , Apr. 18, 2009, 2 pages.
U.S. Appl. No. 14/417,076, filed Jan. 23, 2015.
U.S. Appl. No. 14/416,800, filed Jan. 23, 2015.
U.S. Appl. No. 14/416,947, filed Jan. 23, 2015.
U.S. Appl. No. 14/417,073, filed Jan. 23, 2015.

* cited by examiner

INTERNAL OLEFIN SULFONATE COMPOSITION AND CLEANSING COMPOSITION CONTAINING SAME

FIELD OF THE INVENTION

The present invention relates to an internal olefin sulfonate composition useful as a base for a cleansing agent, and to a cleansing composition containing the same.

BACKGROUND OF THE INVENTION

Anionic surfactants, particularly, alkyl sulfates and alkyl polyoxyalkylene sulfates, are excellent in detergency and foaming power, and thus are widely used as cleansing ingredients for domestic or industrial use. An olefin sulfonate, particularly, an internal olefin sulfonate obtained with an internal olefin having a double bond inside an olefin chain, not at its end, as a raw material, has been reported as one of the anionic surfactants.

Such an internal olefin sulfonate is generally obtained by sulfonating an internal olefin through reactions with a gaseous sulfur trioxide-containing gas, followed by neutralization and then hydrolysis of the resulting sulfonic acid. The internal olefin sulfonate is known to have good biodegradability or the like, but is still insufficient in a basic performance as cleansing agents including foamability and foam quality, compared with general-purpose surfactants such as salts of alkyl polyoxyalkylene sulfuric acid esters. Thus, further improvement in such basic performance has been desired. As more people have concerned the water-saving in recent years, the additional value of foam dissipation property in addition to good foamability, foam quality, foaming speed, and foam durability in the presence of model sebum has also been required for use as active ingredients in laundry detergents, dishwashing detergents, shampoos or the like.

Patent Document 1 discloses a specific internal olefin sulfonic acid for the purposes of the solubilizing ability, penetrating ability, and interfacial tension reducing ability. It discloses that when it is used as a shampoo, it lathers well without friction, and achieves an improved feel.

Patent Document 2 describes a specific internal olefin sulfonate for the purposes of improving detergency, and discloses examples of application to shampoos and the like, and Patent Document 3 also describes an aqueous liquid cleansing agent containing a specific internal olefin sulfonate and having a low cloud point.

CITATION LIST

Patent Document

[Patent Document 1] JP-A-2003-81935
[Patent Document 2] U.S. Pat. No. 5,078,916
[Patent Document 3] U.S. Pat. No. 3,708,437

SUMMARY OF THE INVENTION

The present invention provides an internal olefin sulfonate composition comprising (A) an internal olefin sulfonate having 16 carbon atoms and (B) an internal olefin sulfonate having 18-carbon atoms, wherein a mass content ratio (A/B) of component (A) to component (B) is from 75/25 to 90/10, and wherein a mass ratio (hydroxy form/olefin form) of a content of a hydroxy form in the internal olefin sulfonate of the component (A) and the component (B) to a content of an olefin form in the internal olefin sulfonate of the component (A) and the component (B) is from 75/25 to 100/0.

Also, the present invention provides a cleansing composition comprising the aforementioned internal olefin sulfonate composition.

DETAILED DESCRIPTION OF THE INVENTION

However, further improvement is still required for any of the compositions described in the documents to exert good foamability together with good foam quality, foaming speed, foam dissipation property and foam durability in the presence of model sebum at high levels.

Therefore, the present invention is to provide an internal olefin sulfonate composition which can exert good foamability together with good foam quality, foaming speed, foam dissipation property and foam durability in the presence of model sebum at high levels, and to provide a cleansing composition containing the same.

The present inventor studied a length of an aliphatic chain in an internal olefin sulfonate, a ratio thereof and other various conditions, and consequently found that an internal olefin sulfonate composition which satisfies good foamability, together with good foam quality, foaming speed, foam durability in the presence of model sebum and foam dissipation property can be obtained by setting the ratio between an internal olefin sulfonate having 16 carbon atoms and an internal olefin sulfonate having 18 carbon atoms to a predetermined range. On the basis of these findings, the present invention has been completed.

According to the present invention, it can provide an internal olefin sulfonate composition which can exert good foamability together with good volume of foam, foaming speed, foam dissipation property, foam quality, foam durability in the presence of sebum, and volume of foam in the presence of sebum at high levels, and provide a cleansing composition.

Hereinbelow, the present invention will be described in detail.

<Internal Olefin Sulfonate Composition>

The internal olefin sulfonate composition of the present invention includes (A) an internal olefin sulfonate having 16 carbon atoms and (B) an internal olefin sulfonate having 18 carbon atoms, wherein a mass content ratio (A/B) of component (A) to component (B) is from 75/25 to 90/10.

In the present invention, an internal olefin sulfonate is a sulfonate obtained by sulfonating an internal olefin (an olefin having a double bond inside the olefin chain) as the raw material, followed by neutralization and then hydrolysis, as described above. It should be noted that the above internal olefin may also has a broad meaning including a trace amount of so-called α-olefin, in which a double bond is present at the C-1 position of the carbon chain. That is, sulfonation of an internal olefin quantitatively produces β-sultone, some of which are converted into γ-sultone and olefin sulfonic acid, which are further converted into hydroxyalkane sulfonate and olefin sulfonate in the process of neutralization and hydrolysis (for example, J. Am. Oil Chem. Soc. 69, 39 (1992)). Here, the hydroxyl group of the hydroxyalkane sulfonate thus obtained is present inside the alkane chain, and the double bond of the olefin sulfonate is present inside the olefin chain. Also, the product thus obtained is mainly a mixture of the aforementioned substances, some of which may include a trace amount of hydroxyalkane sulfonate having a hydroxyl group at the end of the carbon chain or olefin sulfonate having a double bond at the end of the carbon chain. In the present specification, each of these products and a mixture thereof are collectively referred to as internal olefin sulfonate. Hydroxyalkane sulfonate is referred to as the hydroxy form of an internal olefin sulfonate (hereinbelow, may also be referred to as HAS), and olefin sulfonate is referred to as the olefin form of an internal olefin sulfonate (hereinbelow, may also be referred to as IOS).

The mass content ratio (A/B) of component (A) to component (B) contained in the internal olefin sulfonate composition of the present invention is from 75/25 to 90/10 from the viewpoint of foamability, volume of foam, foaming speed, foam dissipation property, foam quality, foam durability in the presence of sebum, and volume of foam in the presence of sebum, is preferably from 77/23 to 90/10, more preferably from 77/23 to 85/15 from the viewpoint of foaming speed, foam dissipation property, and foam durability in the presence of sebum during washing the hair, as well as foam dissipation property, and foam dissipation property during washing the hand. Also, the mass content ratio (A/B) of component (A) and component (B) is more preferably from 75/25 to 85/15 and even more preferably from 75/25 to 77/23 from the viewpoint of foam quality, and foam durability in the presence of sebum during washing the hair as well as foam quality, foam durability in the presence of sebum during washing the hand. Also, the mass content ratio (A/B) of component (A) and component (B) is more preferably from 80/20 to 90/10 and even more preferably from 85/25 to 90/10 from the viewpoint of foamability, volume of foam, and volume of foam in the presence of sebum during washing the hair, as well as foamability during washing the hand.

The mass content ratio (A/B) of component (A) to component (B) in the internal olefin sulfonate composition is a numerical value measured by a high-performance liquid chromatograph-mass spectrometer (hereinbelow, abbreviated as HPLC-MS). Specifically, an internal olefin sulfonate having 16 carbon atoms and an internal olefin sulfonate having 18 carbon atoms are separated by HPLC, each of which then is identified by analysis with MS. From the HPLC-MS peak area thereof, the mass content ratio (A/B) of component (A) to component (B) in the internal olefin sulfonate is obtained.

The total content of component (A) and component (B) in the internal olefin sulfonate composition of the present invention is preferably 50% by mass or more, more preferably 70% by mass or more, more preferably 80% by mass or more, more preferably 90% by mass or more, more preferably 95% by mass or more, more preferably 96.5% by mass or more, and even more preferably 97% by mass or more from the viewpoint of foamability, volume of foam, foaming speed, foam dissipation property, foam quality, foam durability in the presence of sebum, and volume of foam in the presence of sebum. The upper limit of the total content of component (A) and component (B) is preferably 100% by mass from the viewpoint of foam dissipation property, foam quality, and foam durability in the presence of sebum during washing the hair, as well as foam quality, and foam durability in the presence of sebum during washing the hand.

As is apparent from the aforementioned production method, the sulfonate group in the internal olefin sulfonate of the present invention is present inside the olefin chain or alkane chain. In the present invention, from the viewpoint of foamability, it is preferable that the content of an internal olefin sulfonate in which the sulfonate group is present at the C-2 position of the olefin chain or alkane chain is low, while the content of an internal olefin sulfonate in which the sulfonate group is present further inside is high. It is more preferable that the content of an internal olefin sulfonate in which the sulfonate group is present at the C-2 position of the olefin chain or alkane chain is low, with respect to both of the above internal olefin sulfonates having 16 carbon atoms and 18 carbon atoms.

The content of the internal olefin sulfonate in which a sulfonate group is present at a C-2 position in the internal olefin sulfonate (component (A) and component (B)) having 16 and 18 carbon atoms is preferably 28% by mass or less, more preferably 24% by mass or less, more preferably 23% by mass or less, more preferably 22% by mass or less, more preferably 20% by mass or less, more preferably less than 20% by mass, more preferably 15% by mass or less, and even more preferably 12% by mass or less, in the total content of the component (A) and the component (B), from the viewpoint of foamability, volume of foam, foaming speed, and foam dissipation property during washing the hair, as well as foamability, and foam dissipation property during washing the hand. Also, the content is preferably 5% by mass or more, more preferably 6% by mass or more, more preferably 7% by mass or more, more preferably 10% by mass or more, more preferably 12% by mass or more, more preferably 15% by mass or more, more preferably 20% by mass or more, and even more preferably 22% by mass or more in the total content of the component (A) and the component (B), from the viewpoint of foam quality and foam durability in the presence of sebum, and volume of foam in the presence of sebum during washing the hair, foam quality, and volume of foam in the presence of sebum during washing the hand, as well as cost, productivity.

Then, the content of the internal olefin sulfonate in which a sulfonate group is present at a C-2 position in the internal olefin sulfonate (component (A) and component (B)) having 16 and 18 carbon atoms is, in the total content of the component (A) and the component (B), preferably 5% by mass or more and preferably 28% by mass or less, more preferably 12% by mass or more and 22% by mass or less, more preferably 12% by mass or more and 20% by mass or less, more preferably 15% by mass or more and 20% by mass or less, and even more preferably 15% by mass or more and less than 20% by mass, from the viewpoint of foamability, volume of foam, foaming speed, foam dissipation property, foam quality, foam durability in the presence of sebum, and volume of foam in the presence of sebum during washing the hair, foamability, foam dissipation property, foam quality, and foam durability in the presence of sebum during washing the hand, as well as cost, productivity. Also, the content is preferably 5% by mass or more and preferably 15% by mass or less, more preferably 6% by mass or more and 15% by mass or less, more preferably 7% by mass or more and 15% by mass or less, and even more preferably 7% by mass or more and 12% by mass or less, from the viewpoint of foamability, volume of foam, foaming speed, and foam dissipation property during washing the hair, as well as foamability, and foam dissipation property during washing the hand. Also, the content is preferably 20% by mass or more and 28% by mass or less, more preferably 23% by mass or more and 28% by mass or less, in the total content of the component (A) and the component (B), from the viewpoint of foam quality, foam durability in the presence of sebum, and volume of foam in the presence of sebum during washing the hair, foam quality, foam durability in the presence of sebum during washing the hand, as well as cost, productivity.

Also, the content of the α-olefin sulfonate in which the sulfonate group is positioned at the C-1 position of an olefin chain or an alkane chain is, in the total content of the component (A) and the component (B), preferably less than 2.8% by mass, more preferably 0.01% by mass or more and less than 2.8% by mass, more preferably 0.1% by mass or more and less than 2.8% by mass, and even more preferably 0.3% by mass or more and less than 2.8% by mass from the viewpoint of foamability and foam dissipation property.

It should note that the content of the internal olefin sulfonate in which the sulfonate group is present at the C-2 position in the internal olefin sulfonate having 16 and 18 carbon atoms may be measured by a method such as nuclear magnetic resonance spectroscopy. More specifically, it is a numerical value measured by a method using gas chromatography described later in Example.

The mass content ratio (hydroxy form/olefin form) of the hydroxy form to the olefin form in the internal olefin sulfonate (component (A) and component (B)) having 16 and 18 carbon atoms is from 75/25 to 100/0, preferably 75/25 to 95/5, more preferably from 80/20 to 95/5 from the viewpoint of foamability, volume of foam, foaming speed, foam dissipation property, foam quality, foam durability in the presence of sebum, and volume of foam in the presence of sebum during washing the hair, as well as foamability, foam dissipation property, foam quality, and foam durability in the presence of sebum during washing the hand.

The mass content ratio of the hydroxy form to the olefin form in the internal olefin sulfonate having 16 and 18 carbon atoms of the present invention may be measured by the method described later in Examples.

As the internal olefin sulfonate composition of the present invention is obtained by sulfonating an internal olefin, followed by neutralization and hydrolysis as described above, an unreacted raw material internal olefin and inorganic compounds may remain in the composition. It is preferred that the contents of these components are much smaller.

The content of the raw material internal olefin in the internal olefin sulfonate composition of the present invention is preferably less than 5.0% by mass, more preferably less than 3.0% by mass, more preferably less than 1.5% by mass, and even more preferably less than 1.0% by mass with respect to the amount of the internal olefin sulfonates from the viewpoint of foamability, volume of foam, foaming speed, foam dissipation property, foam quality, foam durability in the presence of sebum, and volume of foam in the presence of sebum during washing the hair, as well as foamability, foam dissipation property, foam quality, and foam durability in the presence of sebum during washing the hand.

The content of the unreacted internal olefin may be measured by a method described later in Examples.

The content of the inorganic compounds in the internal olefin sulfonate composition of the present invention is preferably less than 7.5% by mass, more preferably less than 5.0% by mass, more preferably less than 3.0% by mass, more preferably less than 2.0% by mass, and even more preferably less than 1.6% by mass with respect to the amount of the internal olefin sulfonates from the viewpoint of foamability, volume of foam, foaming speed, foam dissipation property, foam quality, foam durability in the presence of sebum, and volume of foam in the presence of sebum during washing the hair, as well as foamability, foam dissipation property, foam quality, and foam durability in the presence of sebum during washing the hand.

In this context, the inorganic compounds include sulfates and alkali agents. The content of these inorganic compounds may be measured by a potentiometric titration. Specifically, the content may be measured by a method described later in Examples.

The internal olefin sulfonate composition of the present invention may contain a hydroxy form and an olefin form having any number of carbon atoms which are different from that of component (A) and component (B). The numbers of carbon atoms in the hydroxy form and the olefin form other than the component (A) and the component (B) are preferably from 8 to 15, 17 and from 19 to 24, more preferably from 12, 14 and 20, more preferably from 12 and 14, and even more preferably 14 from the viewpoint of foamability, volume of foam, foaming speed, foam dissipation property, foam quality, foam durability in the presence of sebum, and volume of foam in the presence of sebum during washing the hair, as well as foamability, foam dissipation property, foam quality, and foam durability in the presence of sebum during washing the hand. These hydroxy forms and olefin forms having various numbers of carbon atoms are derived from the internal olefin used as a raw material.

The internal olefin sulfonate composition of the present invention may contain other components, for example, water as a medium, a pH adjuster, a viscosity reducing agent, an organic solvent, and polyhydric alcohols, in addition to the components described above.

<Method for Producing Internal Olefin Sulfonate Composition>

The internal olefin sulfonate composition may be produced by sulfonating a raw material internal olefin having 8 to 24 carbon atoms, followed by neutralization and hydrolysis. More specifically, for example, the composition may be produced in accordance with the methods described in U.S. Pat. Nos. 1,633,184 and 2,625,150, and Tenside Surf. Det. 31 (5) 299 (1994), and the like.

As mentioned above, in the present invention, a raw material internal olefin refers to an olefin substantially having a double bond inside the olefin chain. The content of the α-olefin in which a double bond is present at a C-1 position in the raw material internal olefin is preferably less than 2.8% by mass, more preferably 0.01% by mass or more and less than 2.8% by mass, more preferably 0.1% by mass or more and less than 2.8% by mass, and even more preferably 0.3% by mass or more and less than 2.8% by mass from the viewpoint of foamability, volume of foam, foaming speed, foam dissipation property, foam quality, foam durability in the presence of sebum, and volume of foam in the presence of sebum during washing the hair, as well as foamability, foam dissipation property, foam quality, and foam durability in the presence of sebum during washing the hand. From the viewpoint of foamability, volume of foam, foaming speed, foam dissipation property, foam quality, foam durability in the presence of sebum, and volume of foam in the presence of sebum during washing the hair, as well as foamability, foam dissipation property, foam quality, and foam durability in the presence of sebum during washing the hand of the internal olefin sulfonate composition obtained thus, the number of carbon atoms in the internal olefin is preferably from 8 to 24, more preferably from 12 to 20, more preferably from 12 to 18, more preferably from 14 to 18, and even more preferably from 16 to 18. An internal olefin to be used as a raw material may be used singly, or a combination of two or more thereof may be used.

When the internal olefin sulfonate composition is obtained by sulfonating the raw material internal olefin, followed by neutralization and hydrolysis, the content of an internal olefin in which the double bond is present at the C-2 position in the raw material internal olefin is preferably 48% by mass or less, more preferably 40% by mass or less, more preferably 35% by mass or less, more preferably 33% by mass or less, more preferably 30% by mass or less, more preferably 28% by mass or less, more preferably 23% by mass or less, more preferably 20% by mass or less, more preferably less than 20% by mass and even more preferably 18% by mass or less from the viewpoint of foamability, volume of foam, foaming speed, and foam dissipation property during washing the hair, as well as foamability and foam dissipation property during washing the hand. Also, the content is preferably 5% by mass or more, more preferably 7% by mass or more, more preferably 10% by mass or more, more preferably 15% by mass or more, more preferably 20% by mass or more, more preferably 23% by mass or more, more preferably 33% by mass or more, and even more preferably 35% by mass or more, from the viewpoint of foam quality, foam durability in the presence of sebum, and volume of foam in the presence of sebum during washing the hair, foam quality, and volume of foam in the presence of sebum during washing the hand, as well as cost, productivity.

Then, when the internal olefin sulfonate composition is obtained by sulfonating the raw material internal olefin, followed by neutralization and hydrolysis, the content of an internal olefin in which the double bond is present at the C-2 position in the raw material internal olefin is preferably 5% by mass or more and 48% by mass or less, more preferably 15% by mass or more and 48% by mass or less, more preferably 18% by mass or more and 40% by mass or less, and even more preferably 20% by mass or more and 35% by mass or less, from the viewpoint of foamability, volume of foam, foaming speed, foam dissipation property, foam quality, volume of foam in the presence of sebum, and foam durability in the presence of sebum during washing the hair, foamability, foam quality, and volume of foam in the presence of sebum during washing the hand, as well as cost, productivity. Also, the content is preferably 5% by mass or more and 23% by mass or less, more preferably 7% by mass or more and 23% by mass or less, more preferably 10% by mass or more and 20% by mass or less, more preferably 10% by mass or more and less than 20% by mass, and even more preferably 15% by mass or more and 18% by mass or less from the viewpoint of foamability, volume of foam, foaming speed, foam dissipation property, and foam durability in the presence of sebum during washing the hair, as well as foamability during washing the hand. Also, the content is preferably 33% by mass or more and 48% by mass or less, more preferably 35% by mass or more and 48% by mass or less, and even more preferably 40% by mass or more and 48% by mass or less from the viewpoint of foam quality, foam durability in the presence of sebum, and volume of foam in the presence of sebum during washing the hair, foam quality, volume of foam in the presence of sebum during washing the hand, as well as cost, productivity.

In the synthesis of the internal olefin sulfonate composition, the content of the raw material internal olefin in which the double bond is present at the C-2 position in the raw material internal olefin may be measured by, for example, a gas chromatograph mass spectrometer (hereinbelow, abbreviated as GC-MS). Specifically, components each having different carbon chain lengths and double bond positions are accurately separated by a gas chromatograph analyzer (hereinbelow, abbreviated as GC), and each component is then analyzed by a mass spectrometer (hereinbelow, abbreviated as MS) to identify the position of double bond. From the resulting numerical value of GC peak area, the fraction of each component is found out.

The raw material internal olefin may contain a paraffin component. The content of the paraffin component is preferably less than 5% by mass and more preferably less than 3% by mass from the viewpoint of foamability, foam dissipation property, foam quality, foam durability in the presence of sebum, and volume of foam in the presence of sebum during washing the hair, as well as foam dissipation property, foam quality, and foam durability in the presence of sebum during washing the hand.

The content of the paraffin component may be measured by, for example, GC-MS.

The sulfonation reaction may be carried out by reacting a sulfur trioxide gas with an internal olefin at a ratio of from 1 to 1.2 moles of sulfur trioxide per mole of the raw material internal olefin. The reactions may be carried out at a reaction temperature of from 20 to 40° C.

Neutralization is carried out by reacting from 1 to 1.5 times the molar amount of an alkaline aqueous solution such as sodium hydroxide, potassium hydroxide, ammonia or 2-aminoethanol with the theoretical value of sulfonate group.

The hydrolysis reaction may be carried out at from 90 to 200° C. for from 30 minutes to three hours in the presence of water. These reactions may be successively carried out. Also, upon completion of the reactions, the products may be purified by extraction, washing, or the like.

Also, in the production of the internal olefin sulfonate composition, the raw material internal olefin in which the number of carbon atoms is distributed in from 8 to 24 may be subjected to sulfonation, neutralization, and hydrolysis, or the raw material internal olefin having a uniform number of carbon atoms may be subjected to sulfonation, neutralization, and hydrolysis. Also, a plurality of internal olefin sulfonates each having different numbers of carbon atoms may be produced in advance and then mixed, as needed.

The internal olefin sulfonate composition of the present invention exerts good foamability together with good volume of foam, foaming speed, foam dissipation property, foam quality, foam durability in the presence of sebum, and volume of foam in the presence of sebum at high levels, and is thus useful as a cleansing ingredient. Specifically, the internal olefin sulfonate composition of the present invention can be used in household cleansing agents such as hair shampoos, body cleansers, laundry detergents, and kitchen detergents, and is particularly useful as a base for the hair shampoo.

<Cleansing Composition>

The cleansing composition of the present invention is not particularly limited as long as the cleansing composition contains the internal olefin sulfonate composition of the present invention. The cleansing composition of the present invention may contain other components depending on the intended purpose. Examples of the other components include other surfactant, a foaming promoting agent, and an auxiliary agent. The content of the internal olefin sulfonate composition in the cleansing composition is preferably from 0.1 to 80% by mass, more preferably from 1 to 50% by mass, and even more preferably from 2 to 30% by mass, in terms of the amount of the internal olefin sulfonates.

The other surfactant is preferably, for example, alkyl sulfate and alkyl polyoxyalkylene sulfate. Examples of the auxiliary agent include, but not particularly limited to, water, polymer, an oil solution, silicone, a moisturizing agent, a viscosity regulator, a preservative, an anti-inflammatory agent, an antioxidant, an ultraviolet absorber, a sequestering agent, a pearlescent agent, a dye, a fragrance, an enzyme, a bleaching agent, a bleach activator, and pH adjuster.

The cleansing composition of the present invention may be produced, for example, by mixing the internal olefin sulfonate composition and the components described above.

Hereinafter, the present invention and preferable embodiments of the present invention will be described.

<1> An internal olefin sulfonate composition comprising (A) an internal olefin sulfonate having 16 carbon atoms and (B) an internal olefin sulfonate having 18 carbon atoms, wherein a mass content ratio (A/B) of component (A) to component (B) is from 75/25 to 90/10, and wherein a mass ratio (hydroxy form/olefin form) of a content of a hydroxy form in the internal olefin sulfonate of the component (A) and the component (B) to a content of an olefin form in the internal olefin sulfonate of the component (A) and the component (B) is from 75/25 to 100/0.

<2> The internal olefin sulfonate composition according to <1>, wherein the mass content ratio (A/B) of component (A) to component (B) in the internal olefin sulfonate composition is preferably from 77/23 to 90/10, more preferably from 77/23 to 85/15, and preferably from 75/25 to 85/15, more preferably from 75/25 to 77/23, and preferably from 80/20 to 90/10, more preferably from 85/25 to 90/10.

<3> The internal olefin sulfonate composition according to <1> or <2>, wherein a total content of component (A) and component (B) in the internal olefin sulfonate composition is preferably 50% by mass or more, more preferably 70% by mass or more, more preferably 80% by mass or more, more preferably 90% by mass or more, more preferably 95% by mass or more, more preferably 96.5% by mass or more, and even more preferably 97% by mass or more, with its upper limit being 100% by mass.

<4> The internal olefin sulfonate composition according to any of <1> to <3>, wherein the content of the internal olefin sulfonate in which a sulfonate group is present at a C-2 position in the internal olefin sulfonate (component (A) and component (B)) having 16 and 18 carbon atoms is preferably 28% by mass or less, more preferably 24% by mass or less, more preferably 23% by mass or less, more preferably 22% by mass or less, more preferably 20% by mass or less, even more preferably less than 20% by mass, and preferably 5% by mass or more, more preferably 6% by mass or more, more preferably 7% by mass or more, more preferably 10% by mass or more, more preferably 12% by mass or more, more preferably 15% by mass or more, more preferably 20% by mass or more, and even more preferably 22% by mass or more.

<5> The internal olefin sulfonate composition according to any of <1> to <4>, wherein a content of the internal olefin sulfonate in which a sulfonate group is present at a C-2 position in the internal olefin sulfonate (component (A) and component (B)) having 16 and 18 carbon atoms is preferably 5% by mass or more and preferably 28% by mass or less, more preferably 12% by mass or more and 22% by mass or less, more preferably 12% by mass or more and 20% by mass or less, more preferably 15% by mass or more and 20% by mass or less, and even more preferably 15% by mass or more and less than 20% by mass.

<6> The internal olefin sulfonate composition according to any of <1> to <5>, wherein a content of the internal olefin sulfonate in which a sulfonate group is present at a C-2 position in the internal olefin sulfonate (component (A) and component (B)) having 16 and 18 carbon atoms is preferably 5% by mass or more and preferably 15% by mass or less, more preferably 6% by mass or more and 15% by mass or less, more preferably 7% by mass or more and 15% by mass or less, and even more preferably 7% by mass or more and 12% by mass or less.

<7> The internal olefin sulfonate composition according to any of <1> to <6>, wherein a content of the internal olefin sulfonate in which a sulfonate group is present at a C-2 position in the internal olefin sulfonate (component (A) and component (B)) having 16 and 18 carbon atoms is preferably 20% by mass or more and 28% by mass or less, more preferably 23% by mass or more and 28% by mass or less.

<8> The internal olefin sulfonate composition according to any of <1> to <7>, wherein a mass content ratio of a hydroxy form to an olefin form (hydroxy form/olefin form) in the internal olefin sulfonate having 16 and 18 carbon atoms is preferably from 75/25 to 95/5, more preferably from 80/20 to 95/5.

<9> The internal olefin sulfonate composition according to any of <1> to <8>, wherein a content of a raw material internal olefin in the internal olefin sulfonate composition is preferably less than 5.0% by mass, more preferably less than 3.0% by mass, more preferably less than 1.5% by mass, and even more preferably less than 1.0% by mass with respect to the amount of the internal olefin sulfonates.

<10> The internal olefin sulfonate composition according to any of <1> to <9>, wherein a content of inorganic compounds in the internal olefin sulfonate composition is preferably less than 7.5% by mass, more preferably less than 5.0% by mass, more preferably less than 3.0% by mass, more preferably less than 2.0% by mass, even more preferably less than 1.6% by mass with respect to the amount of the internal olefin sulfonates.

<11> The internal olefin sulfonate composition according to any of <1> to <10>, wherein the numbers of carbon atoms in a hydroxy form and an olefin form having carbon atoms other than component (A) and component (B) in the internal olefin sulfonate composition is preferably from 8 to 15, 17 and from 19 to 24, more preferably from 12, 14 and 20, more preferably from 12 and 14, and even more preferably 14.

<12> The internal olefin sulfonate composition according to any of <1> to <11>, obtained by preferably sulfonating a raw material internal olefin composition containing a raw material internal olefin, followed by neutralization and then hydrolysis, wherein a content of the raw material internal olefin in which a double bond is present at a C-2 position is 48% by mass or less.

<13> The internal olefin sulfonate composition according to any of <1> to <12>, obtained by sulfonating a raw material internal olefin composition containing a raw material internal olefin, followed by neutralization and then hydrolysis, wherein a content of the raw material internal olefin in which a double bond is present at a C-2 position is less than 20% by mass.

<14> The internal olefin sulfonate composition according to any of <1> to <13>, wherein when the internal olefin sulfonate composition is obtained by sulfonating the raw material internal olefin, followed by neutralization and hydrolysis, the content of a raw material internal olefin in which the double bond is present at the C-2 position in the raw material internal olefin is preferably 40% by mass or less, more preferably 35% by mass or less, more preferably 33% by mass or less, more preferably 30% by mass or less, more preferably 28% by mass or less, more preferably 23% by mass or less, more preferably 20% by mass or less, more preferably less than 20% by mass and even more preferably 18% by mass or less.

<15> The internal olefin sulfonate composition according to any of <1> to <14>, wherein when the internal olefin sulfonate composition is obtained by sulfonating the raw material internal olefin, followed by neutralization and hydrolysis, the content of a raw material internal olefin in which the double bond is present at the C-2 position in the raw material internal olefin is preferably 5% by mass or more, more preferably 7% by mass or more, more preferably 10% by mass or more, more preferably 15% by mass or more, more preferably 20% by mass or more, more preferably 23% by mass or more, more preferably 33% by mass or more, and even more preferably 35% by mass or more.

<16> The internal olefin sulfonate composition according to any of <1> to <15>, wherein when the internal olefin sulfonate composition is obtained by sulfonating the raw material internal olefin, followed by neutralization and hydrolysis, the content of a raw material internal olefin in which the double bond is present at the C-2 position in the raw material internal olefin is preferably 5% by mass or more and 48% by mass or less, more preferably 15% by mass or more and 48% by mass or less, more preferably 18% by mass or more and 40% by mass or less, and even more preferably 20% by mass or more and 35% by mass or less.

<17> The internal olefin sulfonate composition according to any of <1> to <16>, wherein when the internal olefin sulfonate composition is obtained by sulfonating the raw material internal olefin, followed by neutralization and hydrolysis, the content of a raw material internal olefin in which the double bond is present at the C-2 position in the raw material internal olefin is preferably 5% by mass or more and 23% by mass or less, more preferably 7% by mass or more and 23% by mass or less, more preferably 10% by mass or more and 20% by mass or less, more preferably 10% by mass or more and less than 20% by mass, and even more preferably 15% by mass or more and 18% by mass or less.

<18> The internal olefin sulfonate composition according to any of <1> to <17>, wherein when the internal olefin sulfonate composition is obtained by sulfonating the raw material internal olefin, followed by neutralization and hydrolysis, the content of a raw material internal olefin in which the double bond is present at the C-2 position in the raw material internal olefin is preferably 33% by mass or more and 48% by mass or less, more preferably 35% by mass or more and 48% by mass or less, and even more preferably 40% by mass or more and 48% by mass or less.

<19> A cleansing composition comprising the internal olefin sulfonate composition according to any of <1> to <18>.

<20> The cleansing composition according to <19>, wherein a content of the internal olefin sulfonate composition is preferably from 0.1 to 80% by mass.

<21> The cleansing composition according to <19> or <20>, further comprising one or more preferably selected from an alkyl sulfate and an alkyl polyoxyalkylene sulfate.

<22> A method for washing hair, comprising applying the cleansing composition of any one of above <19> to <21> to hair, followed by washing and then rinsing.

<23> A method for washing skin, comprising applying the cleansing composition of any one of above <19> to <21> to skin, followed by washing and then rinsing.

<24> A method for improving foam durability in the presence of model sebum, comprising applying the cleansing composition of any one of above <19> to <21> to hair or skin.

<25> A method for improving foam dissipation property and foam quality, comprising applying the cleansing composition of any one of above <19> to <21> to hair or skin.

<26> A method for improving volume of foam, comprising applying the cleansing composition of any one of above <19> to <21> to hair.

<27> The cleansing composition of any one of above <19> to <21> for washing hair.

<28> The cleansing composition of any one of above <19> to <21> for washing skin.

<29> Use of the cleansing composition of any one of above <19> to <21> for washing hair.

<30> Use of the cleansing composition of any one of above <19> to <21> for washing skin.

<31> The cleansing composition of any one of above <19> to <21> for improving foam durability in the presence of model sebum on hair or skin.

<32> Use of the cleansing composition of any one of above <19> to <21> for improving foam durability in the presence of model sebum on hair or skin.

<33> Use of the cleansing composition of any one of above <19> to <21> for improving foam dissipation property and foam quality when applied to hair or skin.

<34> Use of the cleansing composition of any one of above <19> to <21> for improving volume of foam when applied to hair or skin.

EXAMPLES

Hereinbelow, the present invention will be specifically described with reference to Examples. It should be noted that unless otherwise specifically noted, the content of each of the components is expressed by % by mass in the following Tables. Also, the methods for measuring various physical properties are as follows.

(1) Conditions of Measurement
(i) Method for Measuring the Position of a Double Bond in the Internal Olefin The position of a double bond in an internal olefin was measured by gas chromatography (hereinbelow, abbreviated as GC). Specifically, an internal olefin was converted to a dithiated derivative by reaction with dimethyl disulfide, and then each component was separated by GC. The position of a double bond in an internal olefin was found based on the peak area of each component.

The apparatus and analytical conditions used for the measurement are as follows. GC apparatus (trade name: HP6890, the product of Hewlett-Packard Company); Column (trade name: Ultra-Alloy-1HT capillary column, 30 m×250 μm×0.15 μm, the product of Frontier Laboratories Ltd.); Detector (hydrogen flame ionization detector (FID)); Injection temperature of 300° C.; Detector temperature of 350° C.; and He flow rate of 4.6 mL/min.

(ii) Method for Measuring the Content of Internal Olefin Sulfonate in which a Sulfonate Group is Present at a C-2 Position The linkage position of the sulfonate group was measured by GC. Specifically, the internal olefin sulfonate was reacted with trimethylsilyldiazomethane to form a methyl-esterified derivative. Then, each component was separated by GC. Each of a peak area was regarded as a mass ratio, and the content of internal olefin sulfonate in which a sulfonate group is present at a C-2 position was quantitated.

The apparatus and analytical conditions used for the measurement are as follows. GC apparatus (trade name: Agilent technology 6850, the product of Agilent Technologies, Inc.); Column (trade name: HP-1 capillary column, 30 m×320 μm×0.25 μm, the product of Agilent Technologies, Inc.); Detector (hydrogen flame ionization detector (FID)); Injection temperature of 300° C.; Detector temperature of 300° C.; He flow rate of 1.0 mL/min.; oven (60° C. (0 min.)→10° C./min.→300° C. (10 min.)).

(iii) Method for Measuring the Mass Ratio of Hydroxy Form/Olefin Form

The mass ratio of hydroxy form/olefin form was measured by HPLC-MS. Specifically, the hydroxy form and the olefin form were separated by HPLC and each form was identified by separately analyzing with MS. From the resulting HPLC-MS peak area, the fraction of each form was obtained.

The apparatus and analytical conditions used for the measurement are as follows. HPLC apparatus (trade name: Agilent technology 1100, the product of Agilent Technologies, Inc.); Column (trade name: L-column ODS 4.6×150 mm, the product of Chemicals Evaluation and Research Institute, Japan); Sample preparation (diluted 1000-fold with methanol); Eluent A (10 mM ammonium acetate in water); Eluent B (10 mM ammonium acetate in methanol), Gradient (0 min (A/B=30/70%)→10 min (30/70%)→55 min (0/100%)→65 min (0/100%)→66 min (30/70%)→75 min (30/70%)); MS apparatus (trade name: Agilent technology 1100 MS SL (G1946D)); and MS detection (anion detection m/z 60-1600, UV 240 nm).

(iv) Method for Measuring the Content of the Raw Material Internal Olefin

The content of the raw material internal olefin was measured by GC. Specifically, ethanol and petroleum ether were added to an aqueous solution of internal olefin sulfonate, followed by extraction to give olefin in the petroleum ether phase. From the GC peak area of the olefin, the amount thereof was quantitated.

The apparatus and analytical conditions used for the measurement are as follows. GC apparatus (trade name: Agilent technology 6850, the product of Agilent Technologies, Inc.); Column (trade name: Ultra-Alloy-1HT capillary column, 15 m×250 μm×0.15 μm, the product of Frontier Laboratories, Ltd.); Detector (hydrogen flame ionization detector (FID)); Injection temperature of 300° C.; Detector temperature of 350° C.; and He flow rate of 3.8 mL/min.

(v) Method for Measuring the Content of Inorganic Compounds

The content of inorganic compounds was measured by potentiometric titration and neutralization titration. Specifically, the content of $Na_2SO_4$ was quantitated by measuring sulfate ion ($SO_4^{2-}$) by potentiometric titration. Also, the content of NaOH was quantitated by neutralization titration with diluted hydrochloric acid.

(vi) Method for Measuring the Content of the Paraffin Component

The content of the paraffin component was measured by GC. Specifically, ethanol and petroleum ether were added to an aqueous solution of internal olefin sulfonate, followed by extraction to give paraffin in the petroleum ether phase. From the GC peak area of the paraffin, the amount thereof was quantitated.

It should be noted that the apparatus and analytical conditions used are the same as those used for the measurement of the content of the raw material internal olefin.

(2) Production of an Internal Olefin

[Production Example A] Synthesis of C16 Internal Olefins in which 16.5% by Mass of Double Bonds was Present at C-2 Position Into a flask with a stirrer, 7000 g (28.9 moles) of 1-hexadecanol (trade-name: KALCOL 6098, the product of Kao Corporation), and as a solid acid catalyst, 700 g (10% by mass relative to the raw material alcohol) of γ-alumina (STREM Chemicals, Inc.) were placed, and reactions were allowed to proceed for five hours at 280° C. while stirring and passing nitrogen (7000 mL/minute) through the system. The alcohol conversion ratio was 100% and the purity of C16 internal olefin was 99.7% after the completion of the reaction. The resulting crude internal olefin was transferred to a distillation flask and distilled at from 136 to 160° C./4.0 mmHg, whereby 100% pure internal olefin having 16 carbon atoms was obtained. The double bond distribution in the resulting internal olefin was 0.5% by mass at C-1 position, 16.5% by mass at C-2 position, 15.4% by mass at C-3 position, 16.4% by mass at C-4 position, 17.2% by mass at C-5 position, 14.2% by mass at C-6 position, and 19.8% by mass in total at C-7 and 8 positions.

[Production Example B] Synthesis of C18 Internal Olefins in which 16.9% by Mass of Double Bonds was Present at C-2 Position Into a flask with a stirrer, 7000 g (25.9 moles) of 1-octadecanol (trade name: KALCOL 8098, the product of Kao Corporation), and as a solid acid catalyst, 1050 g (15% by mass relative to the raw material alcohol) of γ-alumina (STREM Chemicals, Inc.) were placed, and reactions were allowed to proceed for 13 hours at 285° C. while stirring and passing nitrogen (7000 mL/minute) through the system. The alcohol conversion ratio was 100% and the purity of C18 internal olefin was 98.5% after the completion of the reaction. The resulting crude internal olefin was transferred to a distillation flask and distilled at from 148 to 158° C./0.5 mmHg, whereby 100% pure internal olefin having 18 carbon atoms was obtained. The double bond distribution in the resulting internal olefin was 0.7% by mass at C-1 position, 16.9% by mass at C-2 position, 15.9% by mass at C-3 position, 16.0% by mass at C-4 position, 14.7% by mass at C-5 position, 11.2% by mass at C-6 position, 10.2% by mass at C-7 position, and 14.6% by mass in total at C-8 and 9 positions.

[Production Example C] Synthesis of C16 Internal Olefins in which 30.4% by Mass of Double Bonds was Present at C-2 Position Into a flask with a stirrer, 7000 g (28.9 moles) of 1-hexadecanol (trade-name: KALCOL 6098, the product of Kao Corporation), and as a solid acid catalyst, 700 g (10% by mass relative to the raw material alcohol) of γ-alumina (STREM Chemicals, Inc.) were placed, and reactions were allowed to proceed for three hours at 280° C. while stirring and passing nitrogen (7000 mL/minute) through the system. The alcohol conversion ratio was 100% and the purity of C16 internal olefin was 99.6% after the completion of the reaction. The resulting crude internal olefin was transferred to a distillation flask and distilled at from 136 to 160° C./4.0 mmHg, whereby 100% pure internal olefin having 16 carbon atoms was obtained. The double bond distribution in the resulting internal olefin was 1.8% by mass at C-1 position, 30.4% by mass at C-2 position, 23.9% by mass at C-3 position, 16.8% by mass at C-4 position, 12.0% by mass at C-5 position, 7.4% by mass at C-6 position, and 7.8% by mass in total at C-7 and 8 positions.

[Production Example D] Synthesis of C18 Internal Olefins in which 31.3% by Mass of Double Bonds was Present at C-2 Position Into a flask with a stirrer, 7000 g (25.9 moles) of 1-octadecanol (trade name: KALCOL 8098, the product of Kao Corporation), and as a solid acid catalyst, 700 g (10% by mass relative to the raw material alcohol) of γ-alumina (STREM Chemicals, Inc.) were placed, and reactions were allowed to proceed for 10 hours at 280° C. while stirring and passing nitrogen (7000 mL/minute) through the system. The alcohol conversion ratio was 100% and the purity of C18 internal olefin was 98.2% after the completion of the reaction. The resulting crude internal olefin was transferred to a distillation flask and distilled at from 148 to 158° C./0.5 mmHg, whereby 100% pure purified internal olefin was obtained. The double bond distribution in the resulting internal olefin was 0.8% by mass at C-1 position, 31.3% by mass at C-2 position, 22.9% by mass at C-3 position, 15.5% by mass at C-4 position, 10.8% by mass at C-5 position, 7.2% by mass at C-6 position, 5.3% by mass at C-7 position, and 6.2% by mass in total at C-8 and 9 positions.

[Production Example E] Synthesis of C14 Internal Olefins in which 31.8% by Mass of Double Bonds was Present at C-2 Position A flask with a stirrer was charged with 6000 g (26.7 moles) of 1-tetradecene (product name: LINEALENE 14, the product of Idemitsu Kosan Co., Ltd.) and 180 g (3% by mass relative to the amount of the raw material α-olefin) of protonic β-zeolite (CP-814E, Zeolyst Int.) as a solid acid catalyst, followed by reaction at 120° C. for 20 hours with stirring. Subsequently, the crude internal olefins were transferred to a flask for distillation and distilled at from 124-136° C./7.5 mmHg, to obtain C14 internal olefins having olefin purity of 100%. The double bond distribution of the resulting internal olefins was 1.3% by mass at a C-1 position, 31.8% by mass at a C-2 position, 23.8% by mass at a C-3 position, 21.0% by mass at a C-4 position, 8.6% by mass at a C-5 position, and 13.6% by mass in total at C-6 and C-7 positions.

[Production Example F] Synthesis of C16/18 (Mass Ratio 79.4/20.6) Internal Olefins in which 27.8% by Mass of Double Bonds was Present at C-2 Position A reaction time was adjusted in a same manner as Production Example C, in order to produce C16 internal olefin (double bond distribution was 0.5% by mass at a C-1 position, 30.1% by mass at a C-2 position, 25.5% by mass at a C-3 position, 18.9% by mass at a C-4 position, 11.1% by mass at a C-5 position, 7.0% by mass at a C-6 position, and 7.0% by mass in total at C-7 and C-8 positions). Also, a reaction time was adjusted in a same manner as Production Example D, in order to produce C18 internal olefin (double bond distribution was 0.3% by mass at a C-1 position, 19.0% by mass at a C-2 position, 17.6% by mass at a C-3 position, 17.4% by mass at a C-4 position, 14.9% by mass at a C-5 position, 12.3% by mass at a C-6 position, 8.8% by mass at a C-7 position, and 9.8% by mass in total at C-8 and C-9 positions). 11.9 kg of the resulting C16 internal olefin and 3.1 kg of the resulting C18 internal olefin were mixed to produce 15.0 kg of C16/C18 (mass ratio 79.4/20.6) internal olefin. The double bond distribution of the resulting internal olefin was 0.4% by mass at C-1 position, 27.8% by mass at a C-2 position, 23.9% by mass at a C-3 position, 18.6% by mass at a C-4 position, 11.9% by mass at a C-5 position, 8.1% by mass at a C-6 position, 4.6% by mass at a C-7 position, 3.8% by mass at a C-8 position, and 1.0% by mass at a C-9 position.

[Production Example G] Synthesis of C16/18 (Mass Ratio 79.4/20.6) Internal Olefins in which 45.3% by Mass of Double Bonds was Present at C-2 Position A reaction time was adjusted in a same manner as Production Example C, in order to produce C16 internal olefin (double bond distribution was 2.0% by mass at a C-1 position, 45.9% by mass at a C-2 position, 28.2% by mass at a C-3 position, 13.9% by mass at a C-4 position, 5.5% by mass at a C-5 position, 2.5% by mass at a C-6 position, and 2.2% by mass in total at C-7 and C-8 positions). Also, a reaction time was adjusted in a same manner as Production Example D, in order to produce C18 internal olefin (double bond distribution was 2.1% by mass at a C-1 position, 43.2% by mass at a C-2 position, 29.7% by mass at a C-3 position, 14.9% by mass at a C-4 position, 5.6% by mass at a C-5 position, 3.4% by mass at a C-6 position, 0.9% by mass at a C-7 position, and 0.2% by mass in total at C-8 and C-9 positions). 11.9 kg of the resulting C16 internal olefin and 3.1 kg of the resulting C18 internal olefin were mixed to produce 15.0 kg of C16/C18 (mass ratio 79.4/20.6) internal olefin. The double bond distribution of the resulting internal olefin was 2.1% by mass at a C-1 position, 45.3% by mass at a C-2 position, 28.5% by mass at a C-3 position, 14.1% by mass at a C-4 position, 5.5% by mass at a C-5 position, 2.6% by mass at a C-6 position, 1.0% by mass at a C-7 position, 0.9% by mass at a C-8 position, and 0.02% by mass at a C-9 position.

[Production Example H] Synthesis of C16/18 (Mass Ratio 79.4/20.6) Internal Olefins in which 34.8% by Mass of Double Bonds was Present at C-2 Position A reaction time was adjusted in a same manner as Production Example A, in order to produce C16 internal olefin (a) (double bond distribution was 0.4% by mass at a C-1 position, 15.3% by mass at a C-2 position, 13.7% by mass at a C-3 position, 15.2% by mass at a C-4 position, 18.4% by mass at a C-5 position, 15.1% by mass at a C-6 position, and 21.8% by mass in total at C-7 and C-8 positions). Also, a reaction time was adjusted in a same manner as Production Example C, in order to produce C16 internal olefin (b) (double bond distribution was 2.0% by mass at a C-1 position, 45.9% by mass at a C-2 position, 28.2% by mass at a C-3 position, 13.9% by mass at a C-4 position, 5.5% by mass at a C-5 position, 2.5% by mass at a C-6 position, and 2.2% by mass in total at C-7 and C-8 positions).

In the meantime, a reaction time was adjusted in a same manner as Production Example B, in order to produce C18 internal olefin (a) (double bond distribution was 0.3% by mass at a C-1 position, 13.3% by mass at a C-2 position, 12.6% by mass at a C-3 position, 13.9% by mass at a C-4 position, 14.8% by mass at a C-5 position, 13.7% by mass at a C-6 position, 12.6% by mass at a C-7 position, and 18.8% by mass in total at C-8 and C-9 positions). Also, a reaction time was adjusted in a same manner as Production Example D, in order to produce C18 internal olefin (b) (double bond distribution was 2.1% by mass at a C-1 position, 43.2% by mass at a C-2 position, 29.7% by mass at a C-3 position, 14.9% by mass at a C-4 position, 5.6% by mass at a C-5 position, 3.4% by mass at a C-6 position, 0.9% by mass at a C-7 position, and 0.2% by mass in total at C-8 and C-9 positions). 4.6 kg of the resulting C16 internal olefin (a) and 7.3 kg of the resulting C16 internal olefin (b), and 1.0 kg of the resulting C18 internal olefin (a) and 2.1 kg of the resulting C18 internal olefin (b) were mixed to produce 15.0 kg of C16/C18 (mass ratio 79.4/20.6) internal olefin. The double bond distribution of the resulting internal olefin was 1.9% by mass at a C-1 position, 34.8% by mass at a C-2 position, 23.1% by mass at a C-3 position, 14.4% by mass at a C-4 position, 9.8% by mass at a C-5 position, 7.0% by mass at a C-6 position, 4.4% by mass at a C-7 position, 4.0% by mass at a C-8 position, and 0.6% by mass at a C-9 position.

[Production Example I] Synthesis of C16/18 (Mass Ratio 79.4/20.6) Internal Olefins in which 30.1% by Mass of Double Bonds was Present at C-2 Position A reaction time was adjusted in a same manner as Production Example A, in order to produce C16 internal olefin (c) (double bond distribution was 0.4% by mass at a C-1 position, 15.3% by mass at a C-2 position, 13.7% by mass at a C-3 position, 15.2% by mass at a C-4 position, 18.4% by mass at a C-5 position, 15.1% by mass at a C-6 position, and 21.8% by mass in total at C-7 and C-8 positions). Also, a reaction time was adjusted in a same manner as Production Example C, in order to produce C16 internal olefin (d) (double bond distribution was 0.5% by mass at a C-1 position, 30.1% by mass at a C-2 position, 25.5% by mass at a C-3 position, 18.9% by mass at a C-4 position, 11.1% by mass at a C-5 position, 7.0% by mass at a C-6 position, and 7.0% by mass in total at C-7 and C-8 positions).

In the meantime, a reaction time was adjusted in a same manner as Production Example B, in order to produce C18 internal olefin (c) (double bond distribution was 0.3% by mass at a C-1 position, 13.3% by mass at a C-2 position, 12.6% by mass at a C-3 position, 13.9% by mass at a C-4 position, 14.8% by mass at a C-5 position, 13.7% by mass at a C-6 position, 12.6% by mass at a C-7 position, and 18.8% by mass in total at C-8 and C-9 positions). Also, a reaction time was adjusted in a same manner as Production Example D, in order to produce C18 internal olefin (d) (double bond distribution was 0.5% by mass at a C-1 position, 25.0% by mass at a C-2 position, 22.8% by mass at a C-3 position, 19.1% by mass at a C-4 position, 14.0% by mass at a C-5 position, 7.4% by mass at a C-6 position, 5.4% by mass at a C-7 position, and 5.8% by mass in total at C-8 and C-9 positions). 0.9 kg of the resulting C16 internal olefin (c) and 11.0 kg of the resulting C16 internal olefin (d), and 0.8 kg of the resulting C18 internal olefin (c) and 2.3 kg of the resulting C18 internal olefin (d) were mixed to produce 15.0 kg of C16/C18 (mass ratio 79.4/20.6) internal olefin. The double bond distribution of the resulting internal olefin was 0.9% by mass at a C-1 position, 30.1% by mass at a C-2 position, 24.5% by mass at a C-3 position, 17.3% by mass at a C-4 position, 13.9% by mass at a C-5 position, 6.8% by mass at a C-6 position, 3.2% by mass at a C-7 position, 2.8% by mass at a C-8 position, and 0.4% by mass at a C-9 position.

[Production Example J] Synthesis of C16/18 (Mass Ratio 79.4/20.6) Internal Olefins in which 25.8% by Mass of Double Bonds was Present at C-2 Position A reaction time was adjusted in a same manner as Production Example A, in order to produce C16 internal olefin (e) (double bond distribution was 0.4% by mass at a C-1 position, 15.3% by mass at a C-2 position, 13.7% by mass at a C-3 position, 15.2% by mass at a C-4 position, 18.4% by mass at a C-5 position, 15.1% by mass at a C-6 position, and 21.8% by mass in total at C-7 and C-8 positions). Also, a reaction time was adjusted in a same manner as Production Example C, in order to produce C16 internal olefin (f) (double bond distribution was 0.5% by mass at a C-1 position, 30.1% by mass at a C-2 position, 25.5% by mass at a C-3 position, 18.9% by mass at a C-4 position, 11.1% by mass at a C-5 position, 7.0% by mass at a C-6 position, and 7.0% by mass in total at C-7 and C-8 positions).

In the meantime, a reaction time was adjusted in a same manner as Production Example D, in order to produce C18 internal olefin (e) (double bond distribution was 0.5% by mass at a C-1 position, 25.0% by mass at a C-2 position, 22.8% by mass at a C-3 position, 19.1% by mass at a C-4 position, 14.0% by mass at a C-5 position, 7.4% by mass at a C-6 position, 5.4% by mass at a C-7 position, and 5.8% by mass in total at C-8 and C-9 positions). 3.9 kg of the resulting C16 internal olefin (e) and 8.0 kg of the resulting C16 internal olefin (f), and 3.1 kg of the resulting C18 internal olefin (e) were mixed to produce 15.0 kg of C16/C18 (mass ratio 79.4/20.6) internal olefin. The double bond distribution of the resulting internal olefin was 0.7% by mass at a C-1 position, 25.8% by mass at a C-2 position, 21.6% by mass at a C-3 position, 17.0% by mass at a C-4 position, 15.9% by mass at a C-5 position, 8.5% by mass at a C-6 position, 5.3% by mass at a C-7 position, 4.7% by mass at a C-8 position, and 0.5% by mass at a C-9 position.

[Production Example K] Synthesis of C16/18 (Mass Ratio 79.4/20.6) Internal Olefins in which 22.0% by Mass of Double Bonds was Present at C-2 Position A reaction time was adjusted in a same manner as Production Example A, in order to produce C16 internal olefin (g) (double bond distribution was 0.4% by mass at a C-1 position, 15.3% by mass at a C-2 position, 13.7% by mass at a C-3 position, 15.2% by mass at a C-4 position, 18.4% by mass at a C-5 position, 15.1% by mass at a C-6 position, and 21.8% by mass in total at C-7 and C-8 positions). Also, a reaction time was adjusted in a same manner as Production Example C, in order to produce C16 internal olefin (h) (double bond distribution was 0.5% by mass at a C-1 position, 30.1% by mass at a C-2 position, 25.5% by mass at a C-3 position, 18.9% by mass at a C-4 position, 11.1% by mass at a C-5 position, 7.0% by mass at a C-6 position, and 7.0% by mass in total at C-7 and C-8 positions) and C16 internal olefin (i) (double bond distribution was 0.6% by mass at a C-1 position, 30.6% by mass at a C-2 position, 26.1% by mass at a C-3 position, 18.8% by mass at a C-4 position, 10.5% by mass at a C-5 position, 6.7% by mass at a C-6 position, and 6.6% by mass in total at C-7 and C-8 positions).

In the meantime, a reaction time was adjusted in a same manner as Production Example B, in order to produce C18 internal olefin (f) (double bond distribution was 0.3% by mass at a C-1 position, 13.3% by mass at a C-2 position, 12.6% by mass at a C-3 position, 13.9% by mass at a C-4 position, 14.8% by mass at a C-5 position, 13.7% by mass at a C-6 position, 12.6% by mass at a C-7 position, and 18.8% by mass in total at C-8 and C-9 positions). Also, a reaction time was adjusted in a same manner as Production Example D, in order to produce C18 internal olefin (g) (double bond distribution was 0.5% by mass at a C-1 position, 25.0% by mass at a C-2 position, 22.8% by mass at a C-3 position, 19.1% by mass at a C-4 position, 14.0% by mass at a C-5 position, 7.4% by mass at a C-6 position, 5.4% by mass at a C-7 position, and 5.8% by mass in total at C-8 and C-9 positions). 6.9 kg of the resulting C16 internal olefin (g), 1.2 kg of the resulting C16 internal olefin (h) and 3.8 kg of the resulting C16 internal olefin (i), and 0.8 kg of the resulting C18 internal olefin (f) and 2.3 kg of the resulting C18 internal olefin (g) were mixed to produce 15.0 kg of C16/C18 (mass ratio 79.4/20.6) internal olefin. The double bond distribution of the resulting internal olefin was 0.7% by mass at a C-1 position, 22.0% by mass at a C-2 position, 18.8% by mass at a C-3 position, 16.4% by mass at a C-4 position, 16.3% by mass at a C-5 position, 10.5% by mass at a C-6 position, 7.5% by mass at a C-7 position, 6.9% by mass at a C-8 position, and 0.9% by mass at a C-9 position.

A physical property of the internal olefin obtained by Production Examples A to K as described above is shown in Table 1.

TABLE 1

| | Production Example A | Production Example B | Production Example C | Production Example D | Production Example E | Production ExampleF |
|---|---|---|---|---|---|---|
| Number of carbon atoms of raw material internal olefin (mass ratio in brackets) | 16 | 18 | 16 | 18 | 14 | 16/18 (79.4/20.6) |
| Ratio in which double bond is present at C-2 position (%) | 16.5 | 16.9 | 30.4 | 31.3 | 31.8 | 27.8 |

| | Production ExampleG | Production Example H | Production Example I | Production Example J | Production Example K |
|---|---|---|---|---|---|
| Number of carbon atoms of raw material internal olefin (mass ratio in brackets) | 16/18 (79.4/20.6) | 16/18 (79.4/20.6) | 16/18 (79.4/20.6) | 16/18 (79.4/20.6) | 16/18 (79.4/20.6) |
| Ratio in which double bond is present at C-2 position (%) | 45.3 | 34.8 | 30.1 | 25.8 | 22.0 |

(2) Production of an Internal Olefin Sulfonate

Production Example 1

Using a thin film sulfonation reactor having an outer jacket, the sulfonation reaction of the internal olefin having 16 carbon atoms (the content of an internal olefin in which a double bond is present at a C-2 position is 16.5% by mass) obtained in Production Example A was carried out by passing through sulfur trioxide gas, while passing cooling water of 20° C. through the outer jacket of the reactor. The molar ratio of $SO_3$/internal olefin for the sulfonation reaction was set at 1.09. The resulting sulfonation product was added to an alkaline aqueous solution prepared with 1.5 times the molar amount of sodium hydroxide relative to the theoretical acid value, followed by neutralization at 30° C. for one hour while stirring. The resulting neutralized product was hydrolyzed by heating at 160° C. for one hour in an autoclave, whereby a crude product of sodium C16 internal olefin sulfonate was obtained. Then, 300 g of the crude product was transferred to a separatory funnel, to which 300 mL of ethanol was added and then 300 mL of petroleum ether was added per operation, whereby oil-soluble impurities were removed by extraction. At this time, inorganic compounds (mainly composed of sodium sulfate) which were precipitated at the oil-water interface by the addition of ethanol were also separated and removed from the aqueous phase by the oil-water separation operation. The above removal/extraction operation was repeated three times. Then, the aqueous phase side was evaporated to dryness, whereby sodium C16 internal olefin sulfonate was obtained. The mass ratio of hydroxy form (sodium hydroxyalkane sulfonate)/olefin form (sodium olefin sulfonate) in the obtained sodium internal olefin sulfonate was 81/19. Also, the content of the raw material internal olefin contained in the obtained sodium internal olefin sulfonate was less than 100 ppm (less than GC detection limits), while the content of inorganic compounds therein was 1.3% by mass. Also, the content of an internal olefin sulfonate in which a sulfonate group is present at a C-2 position was 9.3% by mass.

Production Example 2

A sodium C18 internal olefin sulfonate was obtained under the same conditions as those used in Production Example 1 from the internal olefin having 18 carbon atoms (the content of an internal olefin in which a double bond is present at a C-2 position is 16.9% by mass) obtained in Production Example B.

The mass ratio of hydroxy form/olefin form in the obtained sodium internal olefin sulfonate was 80/20. Also, the content of the raw material internal olefin contained in the obtained sodium internal olefin sulfonate was less than 100 ppm (below the GC detection limit) and that of inorganic compounds was 1.7% by mass. Also, the content of an internal olefin sulfonate in which a sulfonate group is present at a C-2 position was 9.6% by mass.

Production Example 3

A sodium C16 internal olefin sulfonate was obtained under the same conditions as those used in Production Example 1 from the internal olefin having 16 carbon atoms (the content of an internal olefin in which a double bond is present at a C-2 position is 30.4% by mass) obtained in Production Example C.

The mass ratio of hydroxy form/olefin form in the obtained sodium internal olefin sulfonate was 90/10. Also, the content of the raw material internal olefin contained in the obtained sodium internal olefin sulfonate was less than 100 ppm (below the GC detection limit) and that of inorganic compounds was 1.9% by mass. Also, the content of an internal olefin sulfonate in which a sulfonate group is present at a C-2 position was 20.3% by mass.

Production Example 4

A sodium C18 internal olefin sulfonate was obtained under the same conditions as those used in Production Example 1 from the internal olefin having 18 carbon atoms (the content of an internal olefin in which a double bond is present at a C-2 position is 31.3% by mass) obtained in Production Example D.

The mass ratio of hydroxy form/olefin form in the obtained sodium internal olefin sulfonate was 80/20. Also, the content of the raw material internal olefin contained in the obtained sodium internal olefin sulfonate was less than 100 ppm (below the GC detection limit) and that of inorganic compounds was 0.9% by mass. Also, the content of an internal olefin sulfonate in which a sulfonate group is present at a C-2 position was 21.4% by mass.

Production Example 5

Using a thin film sulfonation reactor having an external jacket, the sulfonation reaction of the internal olefins having 18 carbon atoms (the content of an internal olefin in which a double bond was present at a C-2 position was 16.9% by mass) obtained in Production Example B was carried out by passing through sulfur trioxide gas, while passing cooling water of 20° C. through the outer jacket of the reactor. The molar ratio of $SO_3$/internal olefin for the sulfonation reaction was set at 1.09. The resulting sulfonation product was transferred to a round-bottom flask and aged by heating at 40° C. for 30 minutes while stirring. Subsequently, the resulting product was added to an aqueous alkali solution prepared with 1.5 times the molar amount of sodium hydroxide relative to the theoretical acid value, followed by neutralization at 30° C. for one hour while stirring. The resulting neutralized product was hydrolyzed by heating at 160° C. for one hour in an autoclave, whereby a crude product of sodium C18 internal olefin sulfonate was obtained. Then, 300 g of the crude product was transferred to a separatory funnel, to which 300 mL of ethanol was added and then 300 mL of petroleum ether was added per operation. The extraction operation was carried out three times. The aqueous phase was evaporated to dryness to obtain a sodium C18 internal olefin sulfonate. The mass ratio of hydroxy form (sodium hydroxyalkane sulfonate)/olefin form (sodium olefin sulfonate) in the obtained sodium internal olefin sulfonate was 57/43. Also, the content of the raw material internal olefin contained in the obtained sodium internal olefin sulfonate was less than 100 ppm (below the GC detection limit), while the content of inorganic compounds therein was 1.2% by mass. Also, the content of an internal olefin sulfonate in which a sulfonate group is present at a C-2 position was 9.6% by mass.

Production Example 6

Synthesis of C14 Internal Olefin Sulfonate

A sodium C14 internal olefin sulfonate was obtained under the same conditions as in Production Example 1 from the internal olefin having 14 carbon atoms (the content of an internal olefin in which a double bond was present at a C-2 position was 31.8% by mass) obtained in Production Example E.

The mass ratio of hydroxy form/olefin form in the obtained sodium internal olefin sulfonate was 93/7. Also, the content of the raw material internal olefin contained in the obtained sodium internal olefin sulfonate was 0% by mass and that of inorganic compounds therein was 0% by mass. Also, the content of an internal olefin sulfonate in which a sulfonate group is present at a C-2 position was 21.7% by mass.

Production Example 7

The composition obtained in Production Example 1 and the composition obtained in Production Example 2 were mixed at a mass ratio of 80:20 to obtain internal olefin sulfonate composition 1.

Production Example 8

The composition obtained in Production Example 1 and the composition obtained in Production Example 2 were mixed at a mass ratio of 90:10 to obtain internal olefin sulfonate composition 2.

Production Example 9

The composition obtained in Production Example 1 and the composition obtained in Production Example 2 were mixed at a mass ratio of 75:25 to obtain internal olefin sulfonate composition 3.

Production Example 10

The composition obtained in Production Example 6, the composition obtained in Production Example 1, and the composition obtained in Production Example 2 were mixed at a mass ratio of 50:40:10 to obtain internal olefin sulfonate composition 4.

Production Example 11

The composition obtained in Production Example 1 and the composition obtained in Production Example 5 were mixed at a mass ratio of 75:25 to obtain internal olefin sulfonate composition 5.

Production Example 12

The composition obtained in Production Example 3 and the composition obtained in Production Example 4 were mixed at a mass ratio of 80:20 to obtain internal olefin sulfonate composition 6.

Production Example 13

The C16/18 internal olefins (the content of internal olefin in which double bonds are present at C-2 position is 27.8% by mass) obtained in Production Example F was used as a raw material, and a sodium C16/C18 internal olefin sulfonate (internal olefin sulfonate composition 7) was obtained by the same manner as in Production Example 1. The mass ratio of hydroxy form (sodium hydroxyalkane sulfonate)/olefin form (sodium olefin sulfonate) in the obtained sodium internal olefin sulfonate was 86/14. Also, the content of the raw material internal olefin contained in the obtained sodium internal olefin sulfonate was less than 100 ppm (below the GC detection limit) and that of inorganic compounds was 1.2% by mass. Also, the content of an internal olefin sulfonate in which a sulfonate group is present at a C-2 position was 17.6% by mass.

Production Example 14

The composition obtained in Production Example 3 and the composition obtained in Production Example 4 were mixed at a mass ratio of 90:10 to obtain internal olefin sulfonate composition 8.

Production Example 15

The composition obtained in Production Example 3 and the composition obtained in Production Example 4 were mixed at a mass ratio of 75:25 to obtain internal olefin sulfonate composition 9.

Production Example 16

The composition obtained in Production Example 6, the composition obtained in Production Example 3, and the composition obtained in Production Example 4 were mixed at a mass ratio of 50:40:10 to obtain internal olefin sulfonate composition 10.

Production Example 17

The C16/18 internal olefins (the content of internal olefin in which double bonds are present at C-2 position is 45.3% by mass) obtained in Production Example G was used as a raw material, and a sodium C16/C18 internal olefin sulfonate (internal olefin sulfonate composition 11) was obtained by the same manner as in Production Example 1. The mass ratio of hydroxy form (sodium hydroxyalkane sulfonate)/olefin form (sodium olefin sulfonate) in the obtained sodium internal olefin sulfonate was 92/8. Also, the content of the raw material internal olefin contained in the obtained sodium internal olefin sulfonate was less than 100 ppm (below the GC detection limit) and that of inorganic compounds was 0.3% by mass. Also, the content of an internal olefin sulfonate in which a sulfonate group is present at a C-2 position was 25.2% by mass.

Production Example 18

The C16/18 internal olefins (the content of internal olefin in which double bonds are present at C-2 position is 34.8% by mass) obtained in Production Example H was used as a raw material, and a sodium C16/C18 internal olefin sulfonate (internal olefin sulfonate composition 12) was obtained by the same manner as in Production Example 1. The mass ratio of hydroxy form (sodium hydroxyalkane sulfonate)/olefin form (sodium olefin sulfonate) in the obtained sodium internal olefin sulfonate was 93/7. Also, the content of the raw material internal olefin contained in the obtained sodium internal olefin sulfonate was less than 100 ppm (below the GC detection limit) and that of inorganic compounds was 0.3% by mass. Also, the content of an internal olefin sulfonate in which a sulfonate group is present at a C-2 position was 21.1% by mass.

Production Example 19

The C16/18 internal olefins (the content of internal olefin in which double bonds are present at C-2 position is 27.8% by mass) obtained in Production Example F was used as a raw material, and a sodium C16/C18 internal olefin sulfonate (internal olefin sulfonate composition 13) was obtained by the same manner as in Production Example 1. The mass ratio of hydroxy form (sodium hydroxyalkane sulfonate)/olefin form (sodium olefin sulfonate) in the obtained sodium internal olefin sulfonate was 93/7. Also, the content of the raw material internal olefin contained in the obtained sodium internal olefin sulfonate was 0.2% by mass and that of inorganic compounds was 0.0% by mass. Also, the content of an internal olefin sulfonate in which a sulfonate group is present at a C-2 position was 17.8% by mass.

Production Example 20

The C16/18 internal olefins (the content of internal olefin in which double bonds are present at C-2 position is 30.1% by mass) obtained in Production Example I was used as a raw material, and a sodium C16/C18 internal olefin sulfonate (internal olefin sulfonate composition 14) was obtained by the same manner as in Production Example 1. The mass ratio of hydroxy form (sodium hydroxyalkane sulfonate)/olefin form (sodium olefin sulfonate) in the obtained sodium internal olefin sulfonate was 93/7. Also, the content of the raw material internal olefin contained in the obtained sodium internal olefin sulfonate was 0.2% by mass and that of inorganic compounds was 0.4% by mass. Also, the content of an internal olefin sulfonate in which a sulfonate group is present at a C-2 position was 18.0% by mass.

Production Example 21

The C16/18 internal olefins (the content of internal olefin in which double bonds are present at C-2 position is 25.8% by mass) obtained in Production Example J was used as a raw material, and a sodium C16/C18 internal olefin sulfonate (internal olefin sulfonate composition 15) was obtained by the same manner as in Production Example 1. The mass ratio of hydroxy form (sodium hydroxyalkane sulfonate)/olefin form (sodium olefin sulfonate) in the obtained sodium internal olefin sulfonate was 93/7. Also, the content of the raw material internal olefin contained in the obtained sodium internal olefin sulfonate was less than 100 ppm (below the GC detection limit) and that of inorganic compounds was 0.8% by mass. Also, the content of an internal olefin sulfonate in which a sulfonate group is present at a C-2 position was 16.7% by mass.

Production Example 22

The C16/18 internal olefins (the content of internal olefin in which double bonds are present at C-2 position is 22.0% by mass) obtained in Production Example K was used as a raw material, and a sodium C16/C18 internal olefin sulfonate (internal olefin sulfonate composition 16) was obtained by the same manner as in Production Example 1. The mass ratio of hydroxy form (sodium hydroxyalkane sulfonate)/olefin form (sodium olefin sulfonate) in the obtained sodium internal olefin sulfonate was 93/7. Also, the content of the raw material internal olefin contained in the obtained sodium internal olefin sulfonate was 0.2% by mass and that of inorganic compounds was 0.7% by mass. Also, the content of an internal olefin sulfonate in which a sulfonate group is present at a C-2 position was 13.7% by mass.

A physical property of the internal olefin sulfonates obtained by Production Examples 1 to 6 is shown in Table 2, and a physical property of the internal olefin sulfonate compositions 1 to 16 obtained by Production Examples 7 to 22 is shown in Table 3.

TABLE 2

|  |  | Internal olefin sulfonate | | | | | |
|---|---|---|---|---|---|---|---|
|  |  | Production Example 1 | Production Example 2 | Production Example 3 | Production Example 4 | Production Example 5 | Production Example 6 |
| Raw material internal olefin | Production Example | Production Example A | Production Example B | Production Example C | Production Example D | Production Example B | Production Example E |
|  | Number of carbon atoms of raw material internal olefin | 16 | 18 | 16 | 18 | 18 | 14 |
|  | Ratio in which double bond is present at C-2 position (%) | 16.5 | 16.9 | 30.4 | 31.3 | 16.9 | 31.8 |
| Internal olefin sulfonate composition | hydroxy form/olefin form | 81/19 | 80/20 | 90/10 | 80/20 | 57/43 | 93/7 |
|  | % of sulfonate group at C-2 position | 9.3 | 9.6 | 20.3 | 21.4 | 9.6 | 22.0 |
|  | Amount of raw material internal olefin | <100 ppm | <100 ppm | <100 ppm | <100 ppm | 0 | 0 |
|  | Amount of inorganic compound (%) | 1.3 | 1.7 | 1.9 | 0.9 | 1.2 | 0 |

TABLE 3

|  |  | Production Example 7 | Production Example 8 | Production Example 9 | Production Example 10 | Production Example 11 | Production Example 12 |
|---|---|---|---|---|---|---|---|
| Internal olefin sulfonate composition |  | Composition 1 | Composition 2 | Composition 3 | Composition 4 | Composition 5 | Composition 6 |
| Raw material internal olefin | Production Example Number of carbon atoms of raw material internal olefin (mass ratio in brackets) Ratio in which double bond is present at C-2 position (%) |  |  |  |  |  |  |
| Internal olefin sulfonate | hydroxy form/olefin form Ratio in which sulfonate group is present at C-2 position (%) Amount of raw material internal olefin Amount of inorganic compound (%) | Production Example 1/2 = 80/20 (mass ratio) | Production Example 1/2 = 90/10 (mass ratio) | Production Example 1/2 = 75/25 (mass ratio) | Production Example 6/1/2 = 50/40/10 (mass ratio) | Production Example 1/5 = 75/25 (mass ratio) | Production Example 3/4 = 80/20 (mass ratio) |

|  |  | Production Example 13 | Production Example 14 | Production Example 15 | Production Example 16 | Production Example 17 |
|---|---|---|---|---|---|---|
| Internal olefin sulfonate composition |  | Composition 7 | Composition 8 | Composition 9 | Composition 10 | Composition 11 |
| Raw material internal olefin | Production Example | Production Example F |  |  |  | Production Example G |
|  | Number of carbon atoms of raw material internal olefin (mass ratio in brackets) | 16/18 (79.4/20.6) |  |  |  | 16/18 (79.4/20.6) |
|  | Ratio in which double bond is present at C-2 position (%) | 27.8 |  |  |  | 45.3 |
| Internal olefin sulfonate | hydroxy form/olefin form | 86/14 | Production Example 3/4 = 90/10 (mass ratio) | Production Example 3/4 = 75/25 (mass ratio) | Production Example 6/3/4 = 50/40/10 (mass ratio) | 92/8 |
|  | Ratio in which sulfonate group is present at C-2 position (%) | 22.0 |  |  |  | 25.5 |
|  | Amount of raw material internal olefin | <100 ppm |  |  |  | <100 ppm |
|  | Amount of inorganic compound (%) | 1.2 |  |  |  | 0.3 |

|  |  | Production Example 18 | Production Example 19 | Production Example 20 | Production Example 21 | Production Example 22 |
|---|---|---|---|---|---|---|
| Internal olefin sulfonate composition |  | Composition 12 | Composition 13 | Composition 14 | Composition 15 | Composition 16 |
| Raw material internal olefin | Production Example | Production Example H | Production Example F | Production Example I | Production Example J | Production Example K |
|  | Number of carbon atoms of raw material internal olefin (mass ratio in brackets) | 16/18 (79.4/20.6) | 16/18 (79.4/20.6) | 16/18 (79.4/20.6) | 16/18 (79.4/20.6) | 16/18 (79.4/20.6) |
|  | Ratio in which double bond is present at C-2 position (%) | 34.8 | 27.8 | 30.1 | 25.8 | 22.0 |
| Internal olefin sulfonate | hydroxy form/olefin form | 93/7 | 93/7 | 93/7 | 93/7 | 93/7 |
|  | Ratio in which sulfonate group is present at C-2 position (%) | 21.1 | 17.8 | 18.0 | 16.7 | 13.4 |
|  | Amount of raw material internal olefin | <100 ppm | 0.2 | 0.2 | <100 ppm | 0.2 |
|  | Amount of inorganic compound (%) | 0.3 | 0.0 | 0.4 | 0.8 | 0.7 |

<Hair Evaluation>

A hair bundle (hair of a Japanese person free from treatment such as bleach or hair color; approximately 20 cm, 15 g) was cleansed with a plain shampoo shown below. Then, after application of a plain rinse shown in the table below, the hair bundle was rinsed off with tap water to obtain a tress for evaluation.

Each of the internal olefin sulfonate compositions 1 to 16 obtained in Production Examples 7 to 22 was dissolved in ion-exchange water to prepare an aqueous solution (13% by mass) of the internal olefin sulfonate composition. Using these aqueous solutions, five expert panelists evaluated their foamability, foam quality, foaming speeds, and foam dissipation property in accordance with evaluation criteria and evaluation methods shown below (specifically, 1.0 g of each aqueous solution (13% by mass) prepared by using the internal olefin sulfonate compositions shown in Table 6 was applied to the tress for evaluation and subjected to lathering, cleansing, and then rinsing).

Also, in the state that 0.05 ml of model sebum was applied to the hair, foam durability in the presence of model sebum was evaluated by washing them using 1.0 g of the aqueous solution (13% by mass) prepared by using the internal olefin sulfonate compositions shown in Table 6. The model sebum was prepared by uniformly mixing 80/20% by mass of triolein/lanolin at 40° C.

The results are shown in Table 6. Table 7 also shows the evaluation results when using alkyl polyoxyethylene sulfate (AES), α-olefin sulfonate (AOS), and secondary alkyl sulfonate (SAS), instead of the above mentioned internal olefin sulfonate composition.

TABLE 4

(Composition of plain shampoo)

| (Component) | (%) |
|---|---|
| Sodium polyoxyethylene lauryl ether sulfate (42.0% in terms of EMAL E-27C (manufactured by Kao Corp.; 27% by weight of active component)) | 11.3 |
| Coconut oil fatty acid N-methylethanolamide (AMINON C-11S (manufactured by Kao Corp.)) | 3.0 |
| Citric acid | 0.2 |
| Methylparaben | 0.3 |
| Purified water | Balance |
| Total | 100.0 |

(Production of Plain Shampoo)

The components were placed in a beaker, heated to 80° C., and then mixed. After confirmation of uniform dissolution, the mixture was cooled to obtain a plain shampoo.

TABLE 5

(Composition of plain rinse)

| (Component) | (%) |
|---|---|
| Octadecyloxypropyl trimethyl ammonium chloride (6.7% in terms of QUARTAMIN E-80K (manufactured by Kao Corp.; 45% by weight of active component)) | 3.0 |
| Stearyl alcohol (KALCOL 8098 (manufactured by Kao Corp.)) | 6.0 |
| Methylparaben | 0.3 |
| Purified water | Balance |
| Total | 100.0 |

(Production of Plain Rinse)

Octadecyloxypropyl trimethyl ammonium chloride and stearyl alcohol were placed in a beaker (A) and melted by heating to 80° C. Purified water and methylparaben were placed in another beaker (B) and heated to 80° C. with stirring. After confirmation of uniform dissolution, the mixed solution in the beaker (A) was added to the beaker (B) with stirring at 80° C. and emulsified for 30 minutes. The heating was terminated, and it was cooled to room temperature to obtain a plain rinse.

<Evaluation Criteria and Evaluation Methods>

Foamability
5: Foaming properties were very good
4: Foaming properties were good
3: Ordinary foamability (equivalent to Comparative Example 1: AES)
2: Foaming properties were poor
1: Foaming properties were too poor to cleanse hair Foaming Speed
5: Lathering was very quick and facilitated cleansing
4: Lathering was quick
3: Ordinary (equivalent to Comparative Example 1: AES)
2: Lathering was slow
1: Lathering was very slow Foam Quality
5: Foam quality was creamy and very good
4: Foam quality was slightly creamy and good
3: Foam quality was ordinary (equivalent to Comparative Example 1: AES)
2: Foam quality was slightly bubbly and poor
1: Foam quality was bubbly and very poor and hindered cleansing Foam Dissipation Property
5: Foam was very quickly dissipated and easily rinsed
4: Foam was quickly dissipated
3: Ordinary (equivalent to Comparative Example 1: AES)
2: Foam was slowly dissipated
1: Foam was very slowly dissipated and hardly rinsed Foam Durability in the Presence of Model Sebum
5: Foam durability was very good (not feeling a decrease in volume of foam during washing)
4: Foam durability was good (less decrease in volume of foam)
3: Ordinary foam durability (equivalent to Comparative Example 1: AES)
2: Foam durability was poor (remarkable decrease in volume of foam)
1: Foam was not maintained (defoaming was found during washing)

<Hand Wash Evaluation>

Each of the internal olefin sulfonate compositions 1 to 16 obtained in Production Examples 7 to 22 was dissolved in ion-exchange water to prepare an aqueous solution (13% by mass) of the internal olefin sulfonate composition. Using these aqueous solutions, five panelists washed their hands, and evaluated foamability, foam quality, and foam dissipation property in accordance with the following evaluation criteria and evaluation method (specifically, 1.0 g of aqueous solution (13% by mass) prepared by using the internal olefin sulfonate compositions shown in Table 6 was applied to the hands and subjected to lathering, cleansing, and rinsing).

Also, in the state that 0.05 ml of model sebum was applied to the hand, foam durability in the presence of model sebum was evaluated by washing them using 1.0 g of the aqueous solution (13% by mass) prepared by using the internal olefin sulfonate compositions shown in Table 6. The model sebum was prepared by uniformly mixing 80/20% by mass of triolein/lanolin at 40° C.

The results are shown in Table 6. Table 7 also shows the evaluation results when using alkyl polyoxyethylene sulfate (AES), α-olefin sulfonate (AOS), and secondary alkyl sulfonate (SAS), instead of the above mentioned internal olefin sulfonate composition.

<Test on Volume of Foam>

A tress treated in the same way as in the hair evaluation was used. Foam obtained by lathering in the same way as above was placed in a graduated cylinder of 5 cm in diameter made of glass, and the volume of the foam was measured. This operation was repeated three times, and an average thereof (rounded off to the closest whole number) was defined as the volume (mL) of foam. Also, a tress to which model sebum (0.05 ml) is applied was used, and the volume (mL) of foam was measured by the same manner as that of the hair evaluation. The measured value was regarded as volume of foam (mL) in the presence of model sebum.

TABLE 6

| | Internal olefin sulfonate composition | 1 | 2 | 3 | 4 | 5 | 6 |
|---|---|---|---|---|---|---|---|
| | Production Example of internal olefin sulfonate composition | Production Example 7 | Production Example 8 | Production Example 9 | Production Example 10 | Production Example 11 | Production Example 12 |
| Structure | Mass ratio of component (A)/component (B) | C16/18 = 80/20 | C16/18 = 90/10 | C16/18 = 75/25 | C14/16/18 = 50/40/10 | C16/18 = 75/25 | C16/18= 80/20 |
| | Content (% by mass) of component (A) and component (B) | 100 | 100 | 100 | 50 | 100 | 100 |
| | Hydroxy form/olefin form | 80/20 | 80/20 | 80/20 | 80/20 | 75/25 | 88/12 |
| | Content of internal olefin sulfonate in which sulfonate group is present at C-2 position in component (A) and component (B) | 9.4 | 9.3 | 9.4 | 9.4 | 9.4 | 20.6 |
| | Ratio of double bond present at C-2 position in raw material internal olefin | 16.6 | 16.5 | 16.6 | 16.6 | 16.6 | 30.6 |
| Composition | Amount of raw material internal olefin | <100 ppm | <100 ppm | <100 ppm | <100 ppm | <100 ppm | <100 ppm |
| | Amount of inorganic compound (% by mass) | 1.4 | 1.3 | 1.4 | 1.0 | 1.3 | 1.7 |
| Evaluation results | Hair evaluation Foamability | 4.4 | 4.8 | 4.2 | 4.6 | | |
| | Volume of foam | 175 | 190 | 165 | 270 | | |
| | Foaming speed | 4.0 | 4.0 | 3.8 | 4.6 | | |
| | Foam dissipation property | 4.8 | 4.4 | 4.4 | 4.4 | | |
| | Foam quality | 2.8 | 2.4 | 3.0 | 2.2 | | |
| | Foam durability in the presence of model sebum | 3.2 | 3.0 | 3.0 | 2.8 | | |
| | Volume of foam in the presence of model sebum | 72 | 78 | 70 | 98 | | |
| | Hand wash evaluation Foamability | 3.8 | 4.0 | 3.8 | 4.6 | | |
| | Foam dissipation property | 5.0 | 5.0 | 5.0 | 5.0 | | |
| | Foam quality | 3.0 | 2.8 | 3.2 | 2.0 | | |
| | Foam durability in the presence of model sebum | 3.0 | 3.0 | 3.0 | 2.6 | | |

| | Internal olefin sulfonate composition | 7 | 8 | 9 | 10 | 11 |
|---|---|---|---|---|---|---|
| | Production Example of internal olefin sulfonate composition | Production Example 13 | Production Example 14 | Production Example 15 | Production Example 16 | Production Example 17 |
| Structure | Mass ratio of component (A)/component (B) | C16/18 = 79.4/20.6 | C16/18 = 90/10 | C16/18 = 75/25 | C14/16/18 = 50/40/10 | C16/18 = 80/20 |
| | Content (% by mass) of component (A) and component (B) | 100 | 100 | 100 | 50 | 100 |
| | Hydroxy form/olefin form | 86/14 | 89/9 | 87.5/12.5 | 90.5/9.5 | 92/8 |
| | Content of internal olefin sulfonate in which sulfonate group is present at C-2 position in component (A) and component (B) | 17.6 | 20.4 | 20.6 | 21.3 | 25.5 |
| | Ratio of double bond present at C-2 position in raw material internal olefin | 27.8 | 30.5 | 30.6 | 31.2 | 45.3 |
| Composition | Amount of raw material internal olefin | <100 ppm | <100 ppm | <100 ppm | <100 ppm | <100 ppm |
| | Amount of inorganic compound (% by mass) | 1.2 | 1.8 | 1.0 | 0.5 | 0.3 |
| Evaluation results | Hair evaluation Foamability | 4.0 | 4.2 | 3.8 | 4.6 | 3.6 |
| | Volume of foam | 130 | 160 | 130 | 240 | 105 |
| | Foaming speed | 3.6 | 3.8 | 3.6 | 4.4 | 3.0 |
| | Foam dissipation property | 4.8 | 4.4 | 4.4 | 4.6 | 3.6 |
| | Foam quality | 3.4 | 3.0 | 3.2 | 2.4 | 4.0 |
| | Foam durability in the presence of model sebum | 4.6 | 4.4 | 4.6 | 4.2 | 5.0 |
| | Volume of foam in the presence of model sebum | 105 | 110 | 90 | 180 | 105 |
| | Hand wash evaluation Foamability | 3.6 | 4.0 | 3.6 | 4.4 | 3.2 |
| | Foam dissipation property | 5.0 | 5.0 | 5.0 | 5.0 | 3.6 |
| | Foam quality | 3.6 | 3.4 | 3.8 | 2.2 | 4.2 |
| | Foam durability in the presence of model sebum | 4.6 | 4.2 | 4.6 | 4.4 | 5.0 |

TABLE 6-continued

| Internal olefin sulfonate composition | | | 12 | 13 | 14 | 15 | 16 |
|---|---|---|---|---|---|---|---|
| | Production Example of internal olefin sulfonate composition | | Production Example 18 | Production Example 19 | Production Example 20 | Production Example 21 | Production Example 22 |
| Structure | Mass ratio of component (A)/component (B) | | C16/18 = 80/20 | C16/18 = 80/20 | C16/18 = 80/20 | C16/18 = 80/20 | C16/18 = 80/20 |
| | Content (% by mass) of component (A) and component (B) | | 100 | 100 | 100 | 100 | 100 |
| | Hydroxy form/olefin form | | 93/7 | 93/7 | 93/7 | 93/7 | 93/7 |
| | Content of internal olefin sulfonate in which sulfonate group is present at C-2 position in component (A) and component (B) | | 21.1 | 17.8 | 18.0 | 16.7 | 13.4 |
| | Ratio of double bond present at C-2 position in raw material internal olefin | | 34.8 | 27.8 | 30.1 | 25.8 | 22.0 |
| Composition | Amount of raw material internal olefin | | <100 ppm | 0.2 | 0.2 | <100 ppm | 0.2 |
| | Amount of inorganic compound (% by mass) | | 0.3 | 0.0 | 0.4 | 0.8 | 0.7 |
| Evaluation results | Hair evaluation | Foamability | 3.8 | 4.0 | 4.0 | 4.2 | 4.4 |
| | | Volume of foam | 125 | 130 | 135 | 130 | 160 |
| | | Foaming speed | 3.4 | 3.6 | 3.6 | 3.6 | 3.8 |
| | | Foam dissipation property | 4.2 | 4.6 | 4.6 | 4.8 | 4.8 |
| | | Foam quality | 3.8 | 3.6 | 3.6 | 3.6 | 3.2 |
| | | Foam durability in the presence of model sebum | 4.8 | 4.6 | 4.4 | 4.6 | 3.6 |
| | | Volume of foam in the presence of model sebum | 100 | 105 | 100 | 100 | 90 |
| | Hand wash evaluation | Foamability | 3.6 | 3.8 | 3.8 | 3.8 | 3.6 |
| | | Foam dissipation property | 4.6 | 5.0 | 5.0 | 5.0 | 5.0 |
| | | Foam quality | 3.8 | 3.6 | 3.6 | 3.6 | 3.2 |
| | | Foam durability in the presence of model sebum | 4.8 | 4.6 | 4.6 | 4.6 | 4.0 |

TABLE 7

| | | | Reference Comparative Examples | | |
|---|---|---|---|---|---|
| | | | 1 AES*4 | 2 AOS*5 | 3 SAS*6 |
| Evaluation results | Hair evaluation | Foamability | 3.0 | 4.0 | 4.8 |
| | | Volume of foam | 93 | 144 | 200 |
| | | Foaming speed | 3.0 | 3.8 | 3.4 |
| | | Foam dissipation property | 3.0 | 3.8 | 2.8 |
| | | Foam quality | 3.0 | 2.4 | 1.2 |
| | | Foam durability in the presence of model sebum | 3.0 | | |
| | | Volume of foam in the presence of model sebum | 65 | | |
| | Hand wash evaluation | Foamability | 3.0 | 3.0 | 4.0 |
| | | Foam dissipation property | 3.0 | 4.2 | 2.0 |
| | | Foam quality | 3.0 | 2.0 | 1.8 |
| | | Foam durability in the presence of model sebum | 3.0 | | |

*4:Sodium alkyl polyoxyethylene sulfate (AES), manufactured by Kao Corp., EMAL 270S (active component: 70%)
*5:Sodium α-olefin sulfonate (AOS), manufactured by Lion Corp., LIPOLAN LB-440 (active component: 36%)
*6:Secondary sodium alkyl sulfonate (SAS), manufactured by LANXESS K.K., Mersolat H95 (active component: 95%)

INDUSTRIAL APPLICABILITY

The internal olefin sulfonate composition of the present invention exerts good foamability together with good foam quality, foaming speed, foam durability in the presence of model sebum and foam dissipation property at high levels. Thus, the internal olefin sulfonate composition of the present invention can be used suitably in the fields of household cleansing agents such as hair shampoos, body cleansers, laundry detergents, kitchen detergents, and residential detergents, and is also suitable for cosmetic emulsifiers, industrial emulsifiers, industrial cleansing agents or the like.

The invention claimed is:

1. A cleansing composition, comprising:
   an internal olefin sulfonate composition comprising (A) an internal olefin sulfonate having 16 carbon atoms and (B) an internal olefin sulfonate having 18 carbon atoms, wherein a mass content ratio (A/B) of the component (A) to the component (B) contained in the total internal olefin sulfonate composition is from 75/25 to 90/10, and wherein a mass ratio of a content of a hydroxyalkane sulfonate of the component (A) and the component (B) to a content of an olefin sulfonate of the component (A) and the component (B) is from 75/25 to 100/0,
   wherein a total content of (A) the internal olefin sulfonate having 16 carbon atoms and (B) the internal olefin sulfonate having 18 carbon atoms in the internal olefin sulfonate is from 70 to 100% by mass.

2. The cleansing composition according to claim 1, wherein a content of an internal olefin sulfonate in which a sulfonate group is present at a C-2 position in the internal olefin sulfonate of the component (A) and the component (B) is 28% by mass or less.

3. The cleansing composition according to claim 1, wherein a content of an internal olefin sulfonate in which a sulfonate group is present at a C-2 position in the internal olefin sulfonate of the component (A) and the component (B) is less than 20% by mass.

4. The cleansing composition according to claim 1, wherein a content of a raw material internal olefin in the internal olefin sulfonate composition is less than 5.0% by mass with respect to the amount of the internal olefin sulfonates.

5. The cleansing composition according to claim 1, wherein a content of inorganic compounds in the internal olefin sulfonate composition is less than 7.5% by mass with respect to the amount of the internal olefin sulfonates.

6. The cleansing composition according to claim 1, wherein the internal olefin sulfonate composition is obtained by sulfonating a raw material internal olefin composition containing a raw material internal olefin, followed by neutralization and then hydrolysis, a content of the raw material internal olefin in which a double bond is present at a C-2 position being 48% by mass or less.

7. The cleansing composition according to claim 1, wherein the internal olefin sulfonate composition is obtained by sulfonating the raw material internal olefin composition containing the raw material internal olefin, followed by neutralization and then hydrolysis, a content of the raw material internal olefin in which a double bond is present at a C-2 position being less than 20% by mass.

8. The cleansing composition according to claim 1, wherein a content of the internal olefin sulfonate composition is from 0.1 to 80% by mass.

9. The cleansing composition according to claim 1, further comprising an alkyl sulfate, an alkyl polyoxyalkylene sulfate, or mixtures thereof.

10. A method for washing hair, comprising applying the cleansing composition according to claim 1 to hair, followed by washing and then rinsing.

11. A method for washing skin, comprising applying the cleansing composition according to claim 1 to the skin, followed by washing and then rinsing.

12. A method for improving foam durability in the presence of model sebum, comprising applying the cleansing composition according to claim 1 to hair or skin.

13. The cleansing composition according to claim 1 for washing hair.

14. The cleansing composition according to claim 1 for washing skin.

15. The cleansing composition according to claim 1 for improving foam durability in the presence of model sebum on hair or skin.

16. The cleansing composition according to claim 1, wherein a content of an internal olefin sulfonate in which a sulfonate group is present at a C-2 position in the internal olefin sulfonate of the component (A) and the component (B) is 24% by mass or less.

* * * * *